United States Patent
Yu et al.

(10) Patent No.: US 9,812,597 B2
(45) Date of Patent: Nov. 7, 2017

(54) OPTICAL SENSOR AND MANUFACTURING METHOD THEREOF

(71) Applicant: Personal Genomics, Inc., Grand Cayman (KY)

(72) Inventors: Teng-Chien Yu, Hsinchu (TW); Sheng-Fu Lin, New Taipei (TW); Ming-Sheng Yang, Hsinchu (TW)

(73) Assignee: PERSONAL GENOMICS, INC., Grand Cayman (KY)

( * ) Notice: Subject to any disclaimer, the term of this patent is extended or adjusted under 35 U.S.C. 154(b) by 0 days.

(21) Appl. No.: 14/823,815

(22) Filed: Aug. 11, 2015

(65) Prior Publication Data

US 2016/0049529 A1 Feb. 18, 2016

Related U.S. Application Data

(60) Provisional application No. 62/036,317, filed on Aug. 12, 2014.

(51) Int. Cl.
*H01L 31/0232* (2014.01)
*B82Y 20/00* (2011.01)
(Continued)

(52) U.S. Cl.
CPC ........ *H01L 31/02327* (2013.01); *B82Y 20/00* (2013.01); *G01N 21/648* (2013.01);
(Continued)

(58) Field of Classification Search
CPC .............. H01L 31/02327; B82Y 20/00; G01N 21/6454; G01N 21/7703; G01N 21/648; G02B 6/1226
(Continued)

(56) References Cited

U.S. PATENT DOCUMENTS

| 5,416,861 A | 5/1995 | Koh et al. |
| 7,385,460 B1 | 6/2008 | Wang et al. |

(Continued)

FOREIGN PATENT DOCUMENTS

| EP | 1918693 A1 | 5/2008 |
| EP | 2940504 | 11/2015 |

(Continued)

OTHER PUBLICATIONS

Australian Office Action dated Aug. 4, 2016, as issued in corresponding Australia Patent Application No. 2015213291 (3 pages).
(Continued)

*Primary Examiner* — Bo Fan
(74) *Attorney, Agent, or Firm* — Muncy, Geissler, Olds & Lowe, P.C.

(57) ABSTRACT

Some embodiments of the present disclosure provide an optical sensor. The optical sensor includes a semiconductive substrate. A light sensing region is on the semiconductive substrate. A waveguide region is configured to guide light from a wave insert portion through a waveguide portion and to a sample holding portion. The waveguide portion includes a first dielectric layer including a first refractive index. A second dielectric layer includes a second refractive index. The second refractive index is smaller than the first refractive index. A first interconnect portion is positioned in the waveguide portion, configured to transmit electrical signal from the light sensing region to an external circuit. The sample holding portion is over the light sensing region.

8 Claims, 44 Drawing Sheets

(51) Int. Cl.
*G01N 21/64* (2006.01)
*G01N 21/77* (2006.01)
*G02B 6/122* (2006.01)

(52) U.S. Cl.
CPC ..... *G01N 21/6454* (2013.01); *G01N 21/7703* (2013.01); *G02B 6/1226* (2013.01)

(58) Field of Classification Search
USPC ............. 257/610, 432; 356/491; 385/14, 43; 362/627; 435/6.1
See application file for complete search history.

(56) References Cited

U.S. PATENT DOCUMENTS

| | | | |
|---|---|---|---|
| 2003/0034491 | A1 | 2/2003 | Lempkowski et al. |
| 2003/0113067 | A1 | 6/2003 | Koh et al. |
| 2004/0114868 | A1* | 6/2004 | Roberson ............... B82Y 20/00 385/43 |
| 2005/0046011 | A1 | 3/2005 | Chen et al. |
| 2006/0055042 | A1 | 3/2006 | Klapproth et al. |
| 2006/0197960 | A1* | 9/2006 | Bazylenko ........... G01N 21/253 356/491 |
| 2007/0218613 | A1* | 9/2007 | Lee ..................... H01L 27/1463 438/197 |
| 2008/0285911 | A1* | 11/2008 | Yamamoto ......... G02B 6/12002 385/14 |
| 2010/0055666 | A1 | 3/2010 | Wimberger-Friedl et al. |
| 2010/0065726 | A1 | 3/2010 | Zhong et al. |
| 2010/0111469 | A1 | 5/2010 | Pyo et al. |
| 2010/0119192 | A1 | 5/2010 | Fujikata et al. |
| 2011/0223590 | A1* | 9/2011 | Chiou .................. C12Q 1/6869 435/6.1 |
| 2012/0021525 | A1 | 1/2012 | Fehr et al. |
| 2012/0156100 | A1* | 6/2012 | Tsai .................... G01N 21/6428 422/82.08 |
| 2012/0226118 | A1 | 9/2012 | Delbeke et al. |
| 2013/0148126 | A1 | 6/2013 | Walters et al. |
| 2013/0301300 | A1* | 11/2013 | Duerksen ............. G02B 6/0095 362/627 |
| 2014/0177995 | A1* | 6/2014 | Mohammed ............ G02B 6/36 385/14 |
| 2016/0079451 | A1* | 3/2016 | Ellis-Monaghan ... H01L 31/103 257/432 |

FOREIGN PATENT DOCUMENTS

| | | |
|---|---|---|
| EP | 2940504 A1 | 11/2015 |
| JP | 2001141965 | 5/2001 |
| JP | 2003202442 | 7/2003 |
| JP | 2003344679 A | 12/2003 |
| JP | 2004061799 A | 2/2004 |
| JP | 2013098534 A | 5/2013 |
| JP | 2013524174 A | 6/2013 |
| TW | 201144793 A | 12/2011 |
| WO | WO03/039216 A1 | 5/2003 |
| WO | WO 2009 115847 | 9/2009 |
| WO | WO 2009/115847 A1 | 9/2009 |
| WO | WO 2014 066826 | 5/2014 |
| WO | WO 2014/066826 A1 | 5/2014 |
| WO | WO2014/066826 A1 | 5/2014 |

OTHER PUBLICATIONS

Rongjin Yan et al., "Evanescent Array-Coupled Biosensors to Organic Nanofilms", IEEE Journal of Selected Topics in Quantum Electronics, vol. 15, No. 5, Sep. 1, 2009, pp. 1469-1477.
Rongjin Yan et al., "Immunoassay Demonstration Using a Local Evanescent Array Coupled Biosensor", Proceedings of SPIE, vol. 7559, Feb. 11, 2010, pp. 75590D-75590D-7.
Gibbon M, "Optical Performance of Integrated 1-5 M Grating Wavelength-Demultiplexer on Inp-Based Waveguide", Electronics Letters, vol. 25, No. 21, Oct. 12, 1989, pp. 1441-1442.
Yan et al., "Response of Local Evanescent Array-Coupled Biosensors to Organic Nanofilms", IEEE Journal of Selected Topics in Quantum Electronics, vol. 15, No. 5, Sep./Oct. 2009, pp. 1469-1477.
Yan et al., "Immunoassay demonstration using a local evanescent array coupled biosensor", Optical Fibers and Sensors for Medical Diagnostics and Treatment Applications X, Proc of SPIE, vol. 7559, 2010, pp. 75590D-1-75590D-7.

* cited by examiner

OPTICAL SENSOR AND MANUFACTURING METHOD THEREOF

CROSS REFERENCE TO RELATED APPLICATIONS

This application claims priority of U.S. Provisional Application No. 62/036,317 filed on Aug. 12, 2014 under 35 U.S.C. §119(e), the entire contents of all of which are hereby incorporated by reference.

FIELD

The present disclosure relates to an optical sensor and a method of manufacturing the same.

BACKGROUND

Optical sensors are widely used in various imaging applications and products, such as cameras, scanners, photocopiers, etc. Optical sensors used in various fields of technology are designed for different purposes.

To improve performance and reduce size of the optical sensors, various designs of the optical sensors are employed. One way to evaluate the performance is by measuring quantum efficiency of the optical sensor. Quantum efficiency is a ratio of a number of charge carriers collected by the optical sensor to a number of photons of a given energy incident on the optical sensor. It is a measurement of the optical sensor's electrical sensitivity to light.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
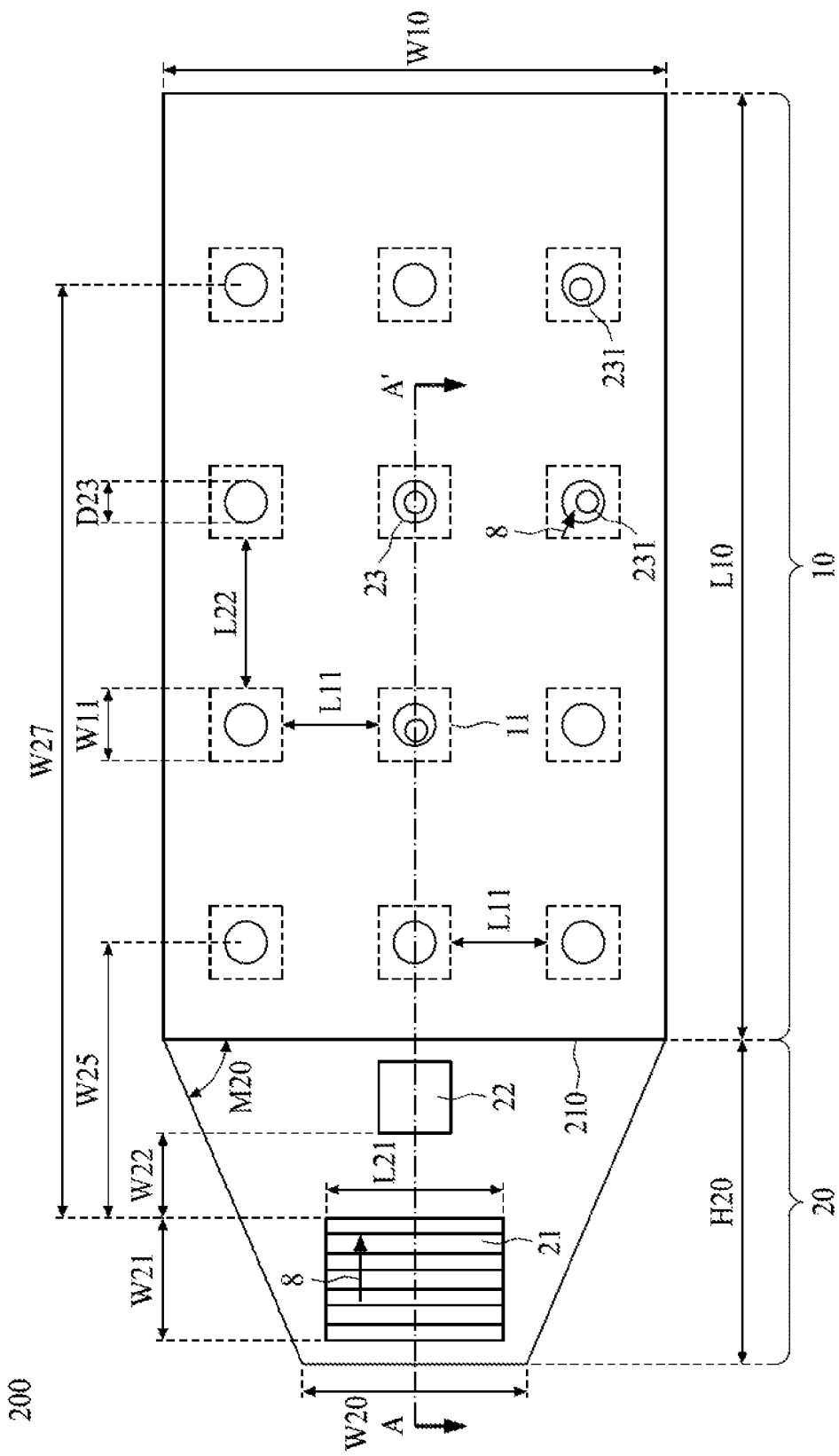
FIG. 1 is a top view of a waveguide region, in accordance with some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

FIG. 1 is a top view of a waveguide region 200 in accordance with some embodiments. The waveguide region 200 includes multilayers. The waveguide region 200 includes an wave insert portion 20 and an optical sensor matrix 10. The wave can be a light wave such as light 8. The wave insert portion 20 includes a grating structure 21 and a pad 22. In some embodiments, the wave insert portion 20 includes a trapezoidal shape. The optical sensor matrix 10 includes an aperture 11 and a sample holding portion 23. The aperture referred herein directs to a transparent path under the sample holding portion 23, allowing a light emitting from the sample to pass through.

In some embodiments, the wave insert portion 20 for receiving a light 8. In some embodiments, the grating structure 21 includes a grating for directing a light 8, such as a laser, traveling towards the optical sensor matrix 10. The light 8 spreads from the wave insert portion 20 toward the optical sensor matrix 10. The light 8 propagates from the grating structure 21 to each sample holding portion 23 of the optical sensor matrix 10. The light 8 shines on a sample 231 in the sample holding portion 23. The sample 231 emits light at a certain wavelength toward the aperture 11. The sample holding portion 23 is also used for holding a specimen 231 which needs to be analyzed.

In some embodiments, the sample holding portion 23 is surrounded in dielectric layers or metal layers. The dielectric layers are transparent to the light 8 from a laser source. The dielectric layers are transparent to the light emitted from the sample 231. Lights 8 of a certain wavelength are allowed to pass through the dielectric layers of the grating structure 21. The grating structure 21 is composed of optical transparent material, such as dielectric material. The grating structure 21 includes material with a certain refractive index. The certain refractive index is variable according to different predetermined optical characteristics of the light 8. The pad 22 is composed of conductive material, such as aluminum, copper, titanium nitride, tungsten, titanium, tantalum, tantalum nitride, nickel silicide, cobalt silicide, TaC, TaSiN, TaCN, TiAl, TiAlN, other suitable materials, and/or combinations thereof. In some embodiments, the pad 22 is a contact pad electrically connecting to other semiconductive components, such as electrical devices.

In some embodiments, a top most layer of the wave insert portion 20 is composed of a reflective layer, such as metal. In some other embodiments, the top most layer of the wave insert portion 20 is composed of a transparent layer, such as a dielectric layer. The sample holding portion 23 is an opening well in the transparent layer. In some embodiments, the aperture 11 is in the reflective layer. The reflective layer is underneath the transparent layer. The reflective layer is below the sample holding portion 23.

The wave insert portion 20 includes a grating structure 21 proximate to the shorter side of the trapezoidal shape. A grating of the grating structure 21 is patterned symmetrically near a center line of the wave insert portion 20. In some embodiments, each line of the grating is spaced evenly. The line of the grating of the grating structure 21 is parallel with the interface 210. The center line is orthogonal to the interface 210. A cross-sectional line AA' divides evenly between the wave insert portion 20 and the optical sensor matrix 10.

The wave insert portion 20 includes a pad 22 proximate to the interface 210. In some embodiments, the pad 22 is disposed between the grating structure 21 and the optical sensor matrix 10, such that the pad 22 is closer to the interface 210. In some other embodiments, the grating structure 21 is between the pad 22 and the optical sensor matrix 10, such that the grating structure 21 is closer to the interface 210.

The optical sensor matrix 10 includes the sample holding portions 23 aligned with the grating structure 21. The sample holding portions 23 are in a row aligned with the center line. In some embodiments, the sample holding portions 23 are disposed symmetrically at either side of the center line.

The sample holding portion 23 includes the opening wells for the specimen to be placed in the sample holding portion 23. The opening well is superimposed on the aperture 11. In some embodiments, the sample holding portion 23 is positioned symmetrically inside the aperture 11. A shape of the opening well can be any suitable shapes, such as a circle or a square. A shape of the aperture 11 can be any suitable shapes, such as a circle or a square. In some embodiments, the area of the aperture 11 is larger than the area of the opening well of the sample holding portion 23.

Figure 2:
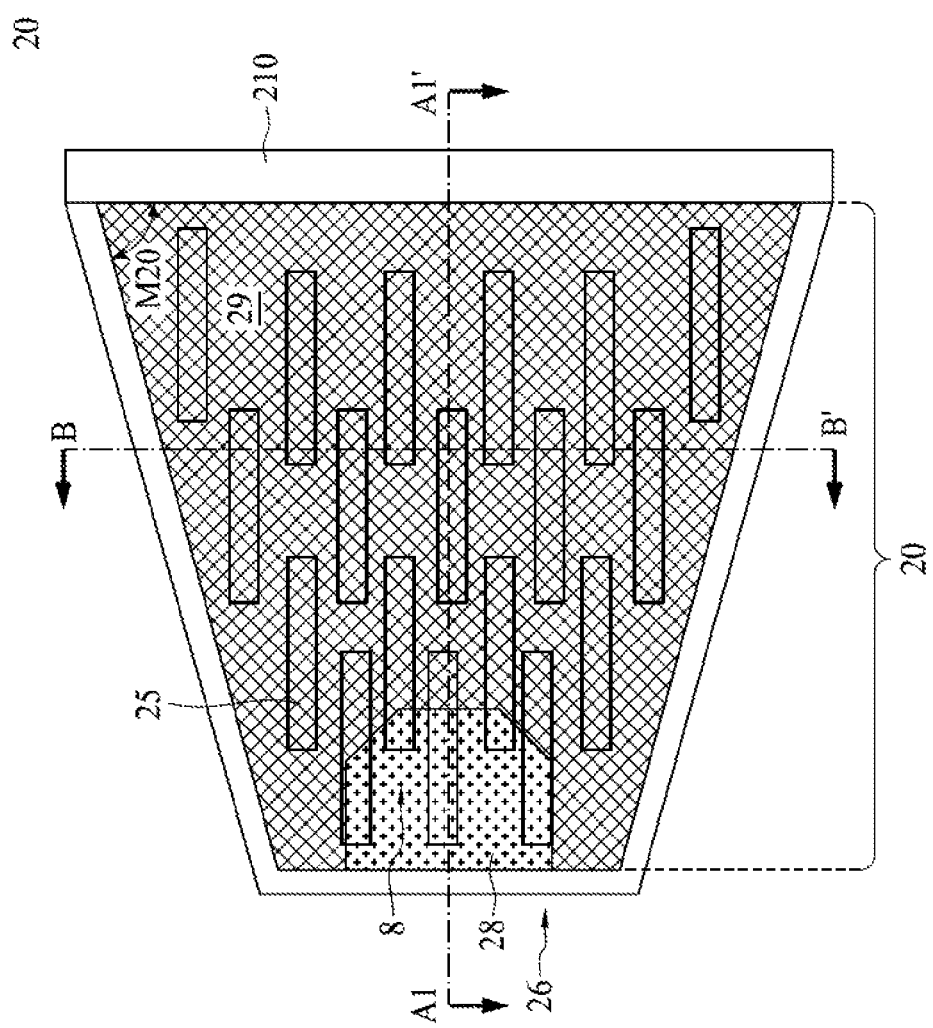
FIG. 2 is a top view of a wave insert portion, in accordance with some embodiments of the present disclosure.

FIG. 2 is a top view of an wave insert portion 20 in accordance with some embodiments. The wave insert portion 20 includes a conductive layer 29 over a dielectric layer 28. The conductive layer 29 includes an opening well 26. A light 8 incidents on the grating structure 21 of the opening well 26, passes through the opening well 26, and travels downward toward the dielectric layer 28. The light 8 travels in the wave insert portion 20 between via structures 25 from the opening well 26 toward the interface 210. Note the via structures 25 can be composed of electrical conductive materials and serve as electrical interconnects in the waveguide region. The interface 210 is between the wave insert portion 20 and the optical sensor matrix 10 in FIG. 1. In some embodiments, the interface 210 includes vias in dielectric layers. The conductive layer 29 and the via structure 25 are composed of reflective material to constrain the light 8 within the wave insert portion 20.

The conductive layer 29 or the via structure 25 are composed of conductive material such as aluminum, copper, titanium nitride, tungsten, titanium, tantalum, tantalum nitride, nickel silicide, cobalt silicide, TaC. TaSiN, TaCN, TiAl, TiAlN, other suitable materials, and/or combinations thereof. The conductive layer 29 and the via structure 25 are composed of highly reflective material in order to guide the light 8 dispersing toward the interface 210.

In some embodiments, the opening well 26 is above the grating structure 21 in FIG. 2. The via structures 25 are distributing throughout the wave insert portion 20. The size and layout of the via structure 25 can be varied according to design considerations. Each via structure 25 is disposed in the wave insert portion 20 according to different design of a circuitry within the wave insert portion 20. The via structures 2 are distributed in the wave insert portion 20 in order to allow the light 8 to pass from the opening well 26 toward the interface 210 with suitable efficiency.

Figure 3:
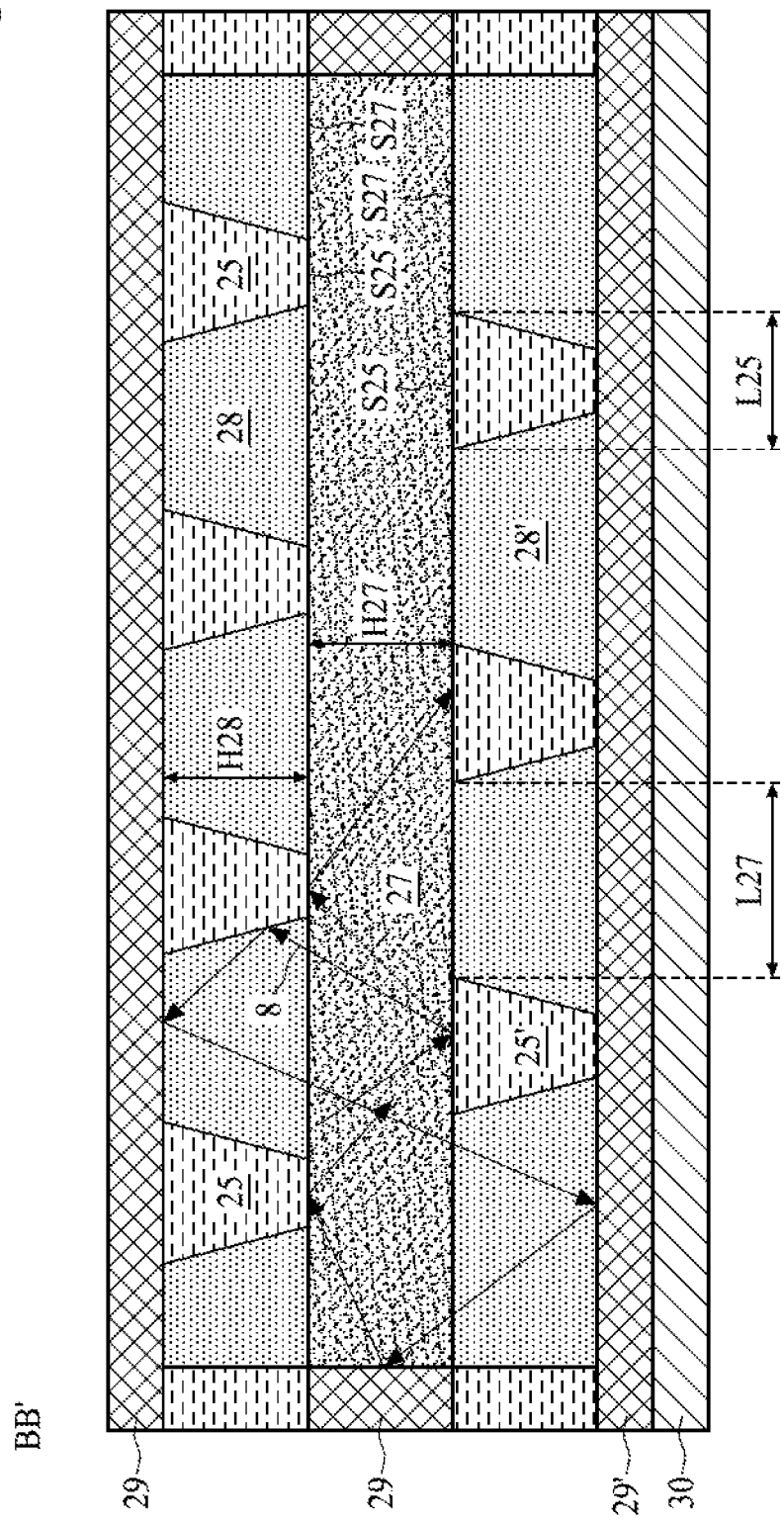
FIGS. 3 and 4 are cross-sectional views of a wave insert portion, in accordance with some embodiments of the present disclosure.

FIG. 3 illustrates a cross-sectional view of an wave insert portion 20 from the cross-sectional line BB' in FIG. 2. In FIG. 3, the light 8 scatters within the wave insert portion 20 through the lower portion. The light 8 reflects off from the via structure 25 or the conductive layer 29. Most of the lights 8 are constrained within the dielectric layer 27. In some embodiments, the dielectric layer 27 is also referred to as a core layer. Dielectric layer 28' and conductive layer 29' are under the dielectric layer 27. Some of the lights 8 reaching the dielectric layer 28' are reflected from the conductive layer 29' back to the dielectric layer 27. In some embodiments, the dielectric layer 28 or the dielectric layer 28' is referred to as a cladding layer. A filter layer 30 is at a bottom of the wave insert portion 20. The filter layer 30 is below the dielectric, layer 28', the dielectric layer 27, and the conductive layer 29'. The filter layer 30 is configured to filter laser light and allow the light emitting from the sample to penetrate through. In some embodiments, the filter layer 30 can enhance the signal to noise ratio of the optical sensor.

In some embodiments, the dielectric layer 27 is a first dielectric layer including a first refractive index. The dielectric layer 28 is a second dielectric layer including a second refractive index. The second refractive index is lower than the first refractive index. When light travels from a first medium with a higher refractive index toward a second medium with a lower refractive index, light is likely to be reflected from the interface there between by a total internal reflection. Similarly, a light 8 traveling from the dielectric layer 27 toward the dielectric layer 28' is likely to be reflected from the dielectric layer 28'. The dielectric layer 28 is above the dielectric layer 27. The dielectric layer 28' is below the dielectric layer 28. With the dielectric layer 27 between the dielectric layer 28 and the dielectric layer 28', a path of a light 8 is likely to be confined within the dielectric, layer 27. In some embodiments, the first refractive index is different from the second refractive index by a predetermined range. A ratio between the first refractive index and the second refractive index is greater than 1.

The conductive layer 29 is above the via structure 25. The via structure 25' is below the dielectric layer 27. The via structure 25 is above the dielectric layer 27. The conductive layer 29' is below a via structure 25. The conductive layer 29 is above the dielectric layer 27. The conductive layer 29' is below the conductive layer 29. The conductive layer 29 is adjacent to a lateral side of the dielectric layer 27.

The via structure 25 can be positioned in the dielectric layer 28 or in the dielectric layer 27. The via structure 25 is in contact with the conductive layer 29. The via structure 25 includes a surface S25 exposed to the dielectric layer 27. The surface S25 is an interface between the dielectric layer 27 and the via structure 25. In some embodiments, areas of surfaces S25 of different via structures 25 are different.

An interface S27 is between the dielectric layer 27 and the dielectric layer 28. A predetermined ratio between a total area of the interface S27 and a total area of the surface S25 can be a design factor according to different applications. In some embodiments, the predetermined ratio is approximately larger than 10. Each surface S25 includes a length L25 from one edge of the via structure 25 to another edge of the same via structure 25. A length L27 of the interface S27 is from one edge of via structure 25 to another edge of another via structure 25. A ratio between the length L27 and the length L25 is predetermined. In some embodiments, areas of the surface S25 of via structures 25 are substantially the same. In some embodiments, the lengths L27 are substantially equal such that the via structures 25 are spaced equally from each other.

Figure 4:
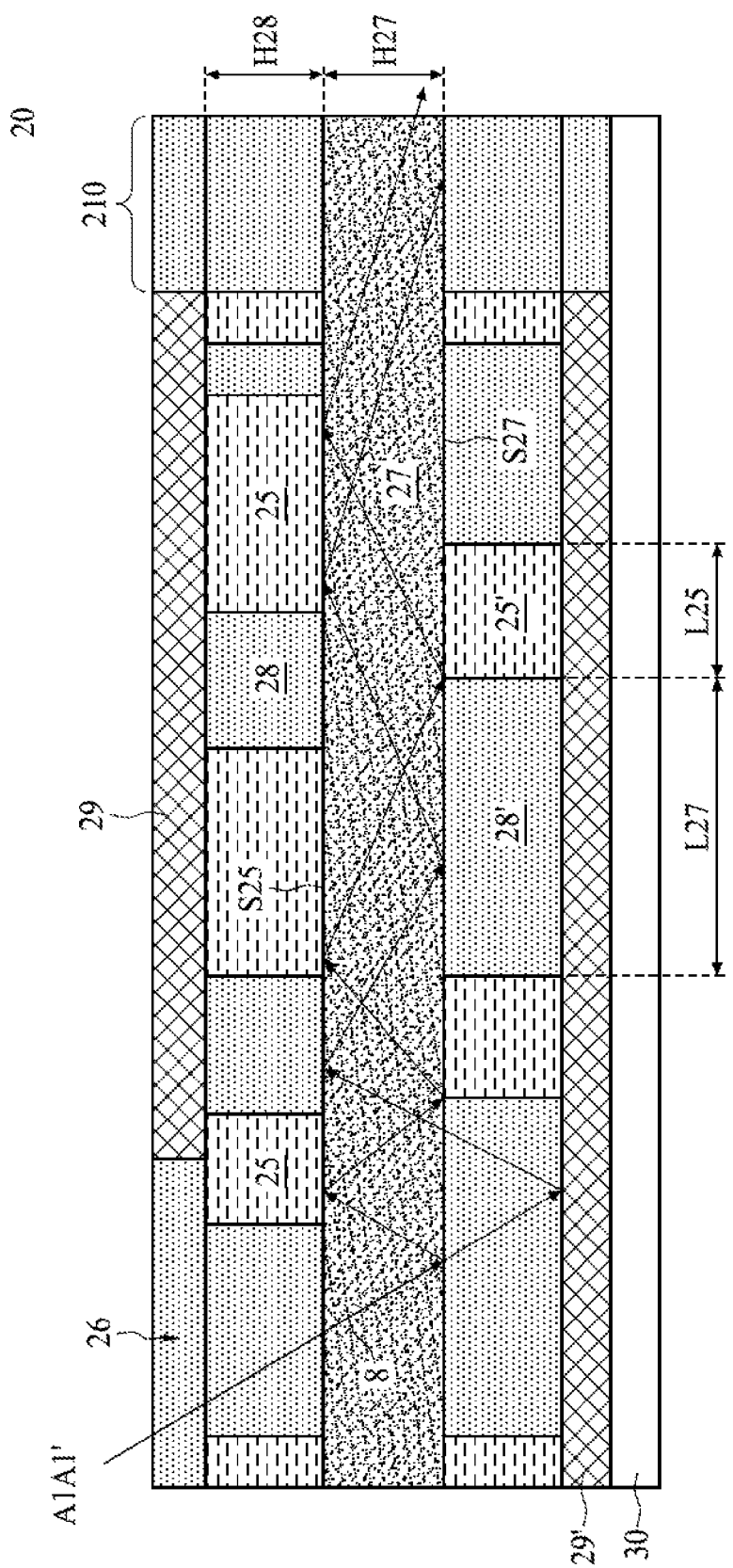

FIG. 4 illustrates a cross-sectional view of the wave insert portion 20 from the cross-sectional line A1A1' in FIG. 2. In FIG. 4, a light 8 coming through the opening well 26 travels down to reach the dielectric layer 27. The conductive layer 29 above the dielectric layer 28 and the dielectric layer 27 is extended up to the opening well 26 in order to expose the dielectric, layer 28 to a light 8 coming from upper layers. In some embodiments, the light 8 propagates from the opening well 26 toward the interface 210. In some embodiments, the conductive layer 29 above the dielectric layer 27 extends up to the interface 210 in order to expose the dielectric, layer 28 at the interface 210. Most of the lights 8 are kept within the dielectric layer 27 inside the core layer.

In some embodiments, the lengths L25 of the via structures 25 are variable from each other such that the via structures 25 includes different area of the surface S25. In some embodiments, the lengths L27 are variable from each other such that the via structures 25 are separated from each other by a different length L27.

Figure 5:
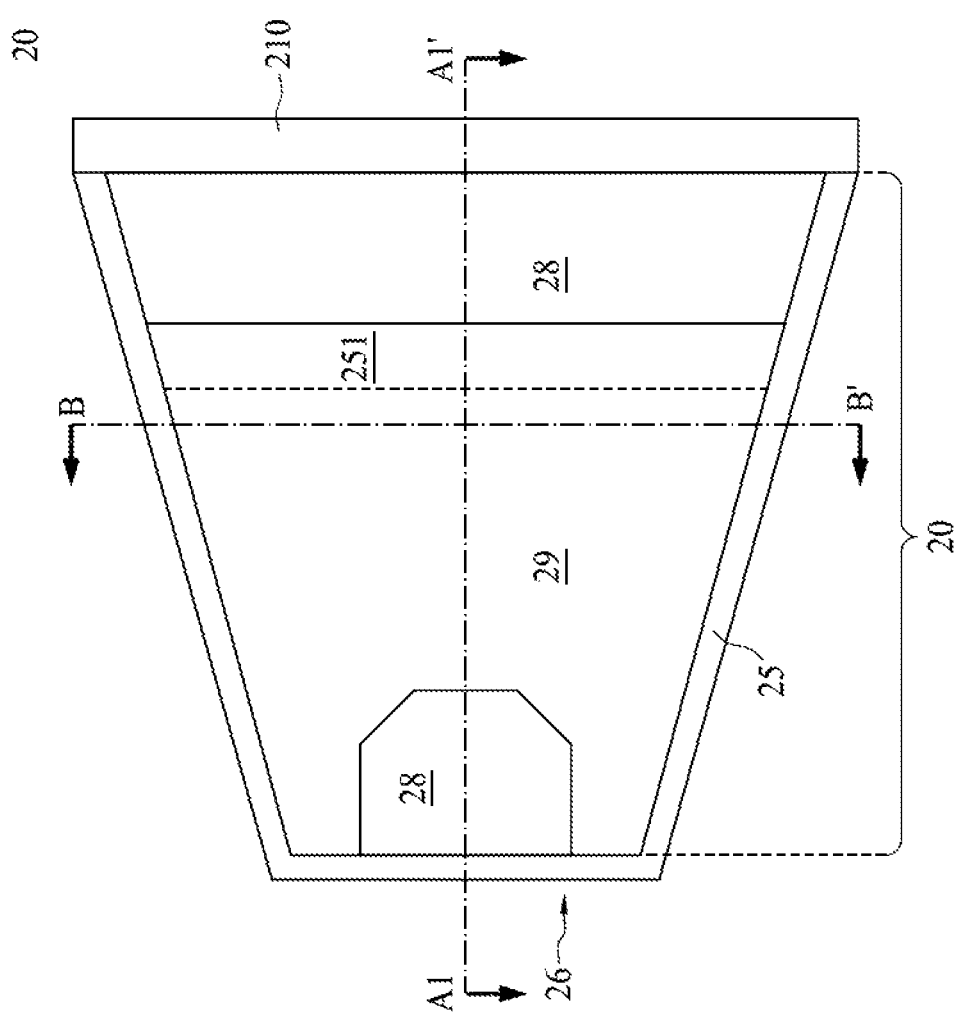
FIG. 5 is a top view of a wave insert portion, in accordance with some embodiments of the present disclosure.

FIG. 5 is similar to FIG. 2, except that in FIG. 2, the wave insert portion 20 includes the via structure 25 inside the dielectric layer 28, while in FIG. 5, in some embodiments, the dielectric layer 28 in the wave insert portion 20 does not include the via structure 25. In FIG. 5, the via structure 25 is aligned with a boundary of the wave insert portion 20. A light 8, such as a laser light, enters a waveguide region 200 through the opening well 26.

Figure 6:
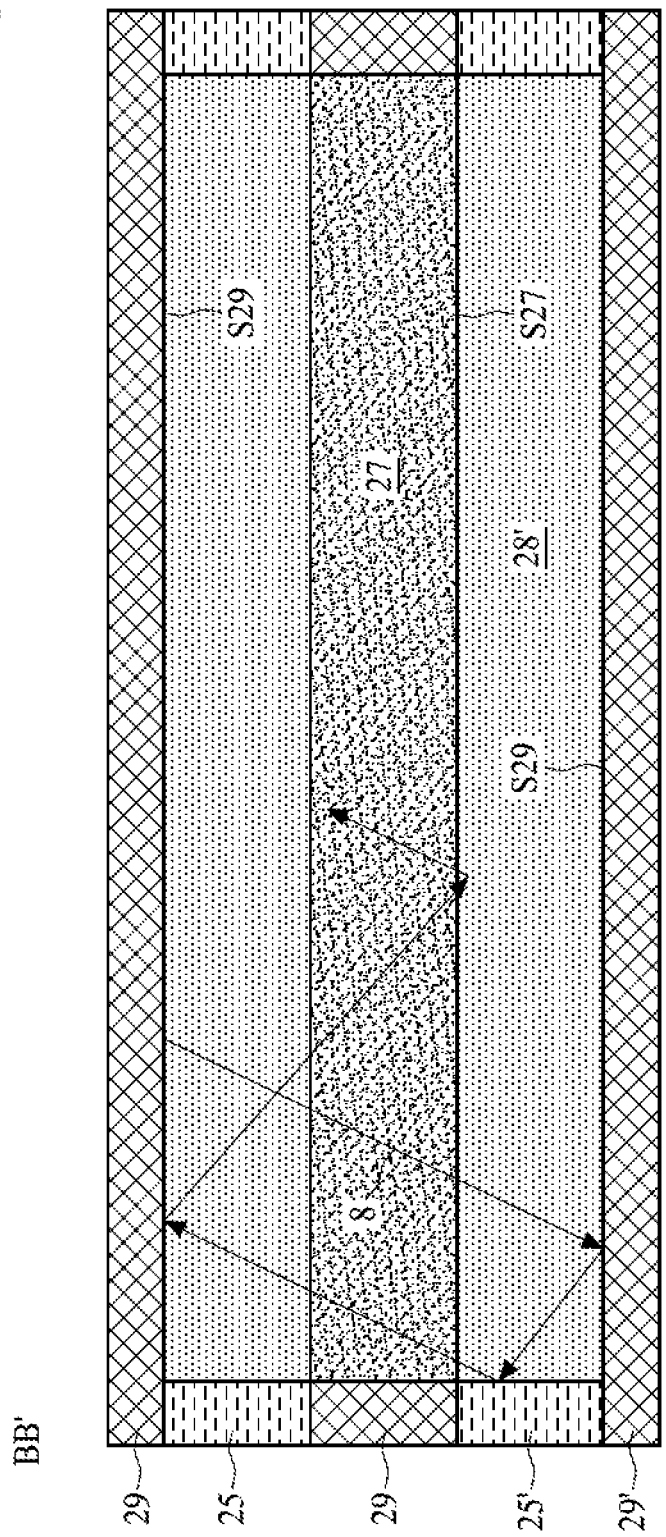
FIGS. 6 and 7 are cross-sectional views of a wave insert portion, in accordance with some embodiments of the present disclosure.

FIG. 6 illustrates a cross-sectional view of the wave insert portion 20 from the cross-sectional line BB' in FIG. 5. In FIG. 6, the light 8 reflects off from the conductive layer 29 above dielectric layer 27 or the conductive layer 29' below the dielectric layer 27. The light 8 reflects off from the via structure 25 at either side of the dielectric layer 28. The light 8 also reflects off from the interface S27 between the dielectric layer 28 and the dielectric layer 27. In some embodiments, the conductive layer 29 or the conductive layer 29' includes a surface S29 facing toward the dielectric layer 27. In FIG. 6, an area of the surface S29 and an area of the interface S27 are substantially equal such that a ratio between the area of the surface S29 and the area of the interface S27 is substantially equals to 1.

Figure 7:
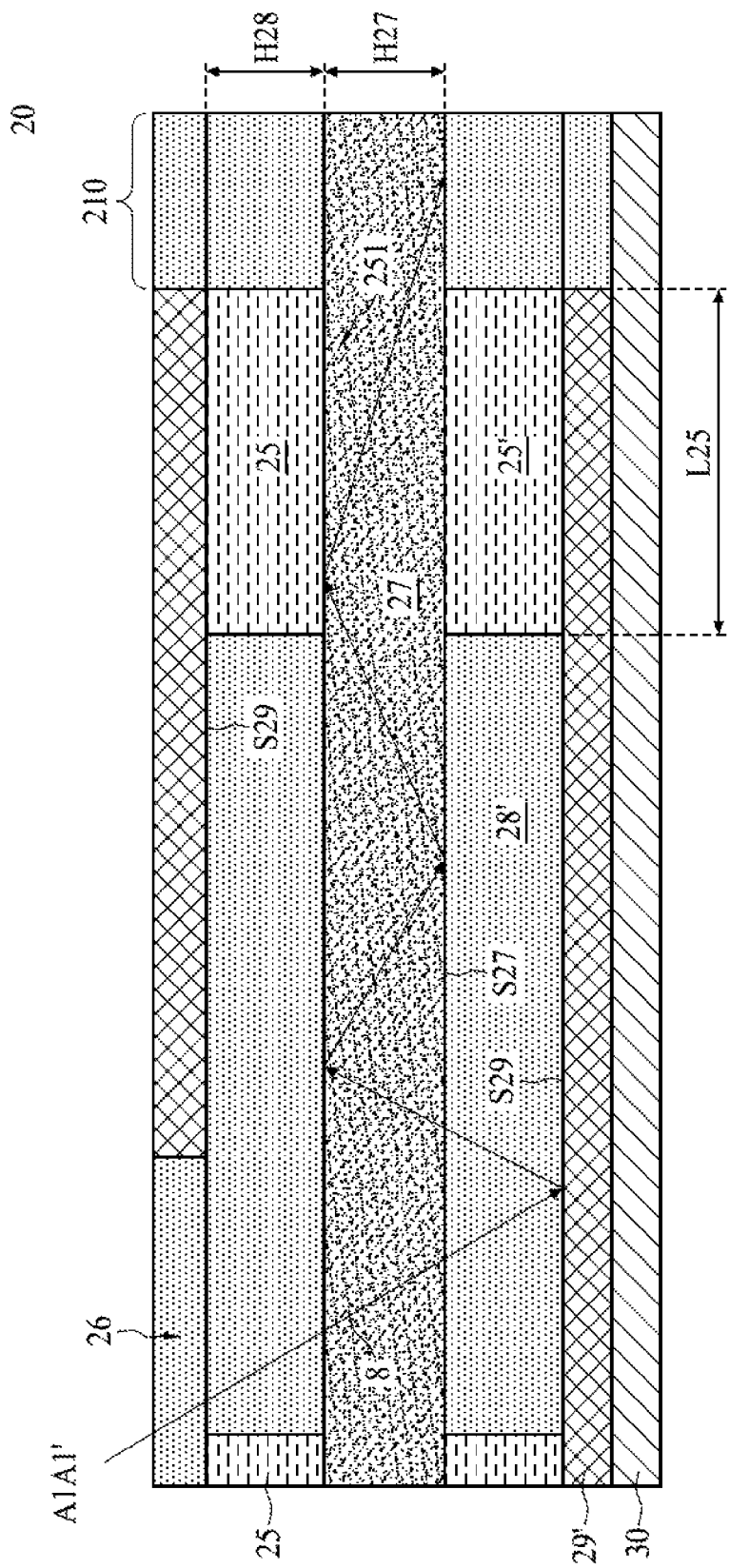

FIG. 7 illustrates a cross-sectional view of the wave insert portion 20 from the cross-sectional line A1A1' in FIG. 5. A light 8 near the interface 210 passes through the opening well 251 before reaching the interface 210. The opening well 251 is a portion of the dielectric layer 27 between via structure 25 and via structure 25' proximate to the interface 210. In some embodiments, a light 8 is dispersed or diffracted when passing through the opening well 251. In FIG. 5, the opening well 251 is illustrated in dotted lines since the opening well 251 is under the conductive layer 29 or the via structure 25.

A thickness of the opening well 251 is substantially equal to the thickness H27 of the dielectric layer 27. A length of the opening well 251 is substantially equal to the length L25 of the via structures 25 over the opening well 251.

The conductive layer 29 above the dielectric layer 27 extends up to the interface 210. The conductive layer 29' below the dielectric, layer 27 also extends up to the interface 210. Most of the lights 8 are confined inside the dielectric layer 27 by the interface S27 or the conductive layer 29 before passing through the opening well 251. A filter layer 30 is at a bottom of the wave insert portion 20. The filter layer 30 is below the dielectric layer 28', the dielectric layer 27, and the conductive layer 29'.

Figure 8:
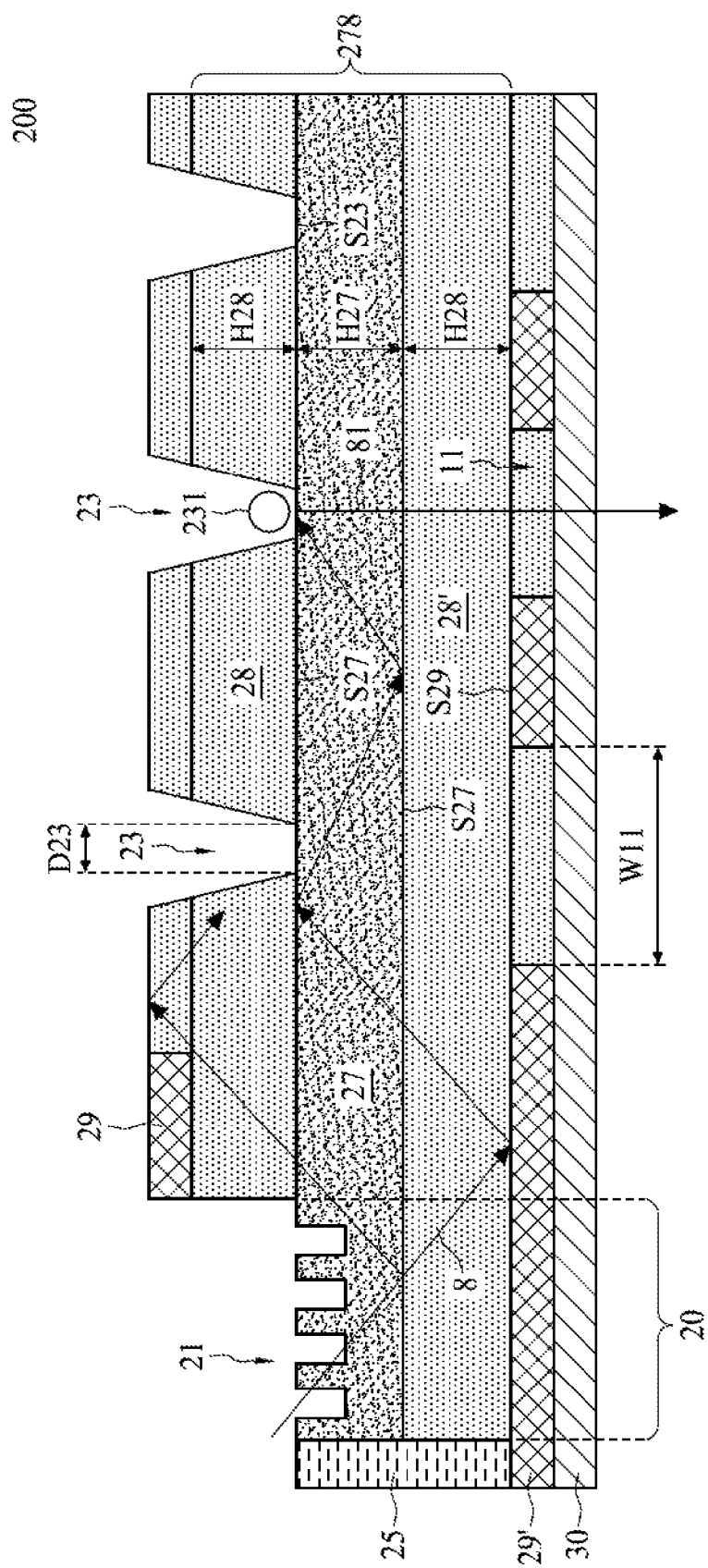
FIGS. 8 to 13 are cross-sectional views of a waveguide region, in accordance with some embodiments of the present disclosure.

FIG. 8 illustrates a cross-sectional view of a waveguide region 200 according to some embodiments. In FIG. 8, the waveguide region 200 includes an wave insert portion 20, a waveguide portion 278, and a sample holding portion 23.

A light 8 passing though the grating structure 21 of the wave insert portion 20 travels through the dielectric layer 28 or the dielectric layer 27 inside the waveguide portion 278 and reaches the sample holding portion 23. The light 8 illuminates on the specimen 231 in the sample holding portion 23. The light 8 propagates from the grating structure 21 to each sample holding portion 23. The sample 231 illuminated by the light 8 reemits light at a certain wavelength toward the aperture 11. In some embodiments, the light 81 is emitted from the specimen or the sample. In some embodiments, the light 81 is different from the light 8 in some optical characteristic, such as wavelength, polarity, or intensity. The light 81 passes through the aperture 11 and through the filter layer 30. The filter layer 30 prevents the light 8, such as a laser from the laser source, from entering into underlying regions. The filter layer 30 allows light emitted from the sample 231, such as the light 81, to pass through toward the underlying regions.

In some embodiments, the conductive layer 29 above the dielectric layer 28 extends up to near the sample holding portion 23. The aperture 11 is in the conductive layer 29. In some embodiments, the conductive layer 29 below the dielectric layer 28' extends up to the aperture 11 to allow the light 81 to pass through the aperture 11. In some embodiments, a second refractive index of the dielectric layer 28 is smaller than a first refractive index of the dielectric layer 27.

In some embodiments, the grating structure 21 includes the grating with an undulating pattern on a top surface of the dielectric layer 27. In some embodiments, the top surface of the grating is exposed to an ambient environment. The sample holding portion 23 is a recess in the dielectric layer 28. The recess of the sample holding portion 23 is surrounded by a portion of the dielectric layer 28. The recess exposes an underlying surface of the dielectric layer 27.

Figure 9:
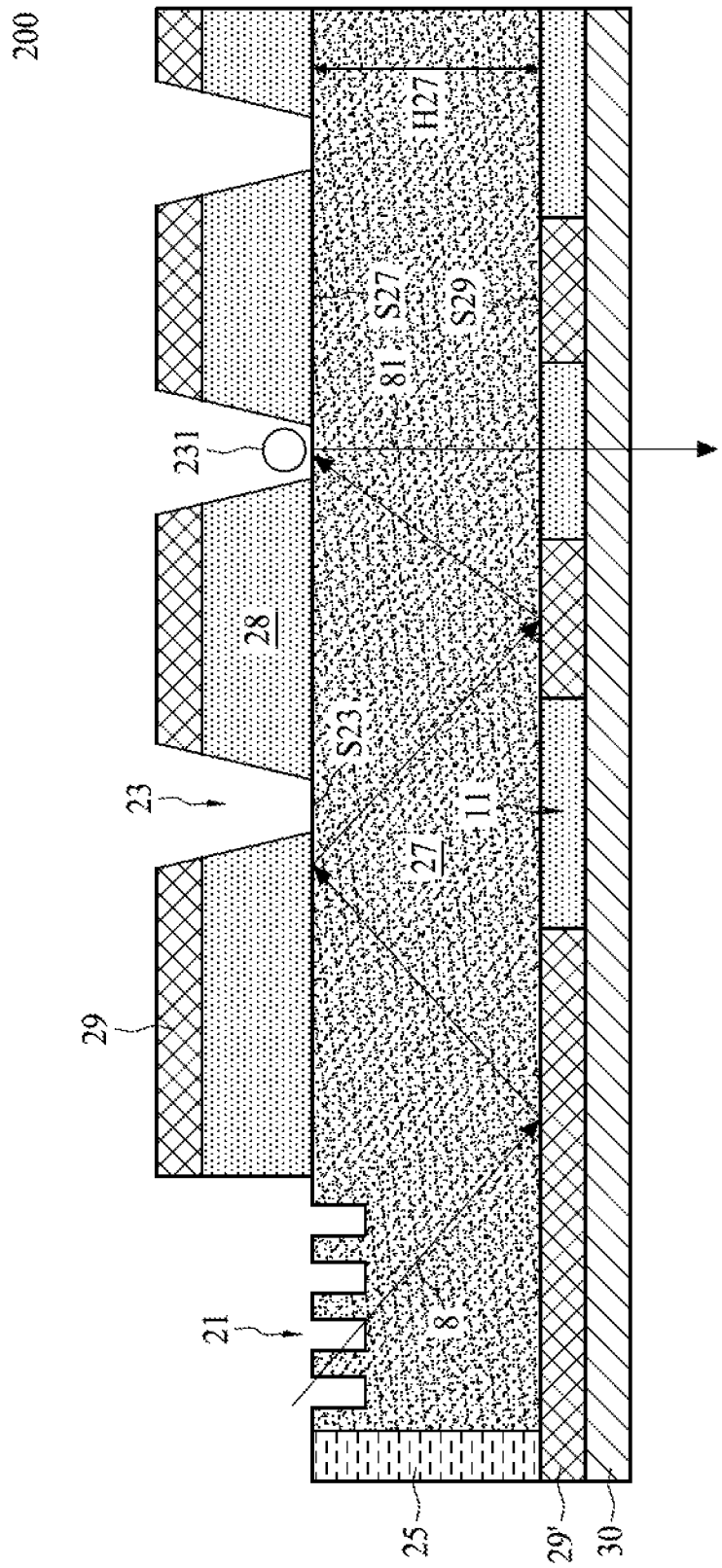

FIG. 9 illustrates a cross-sectional view of a waveguide region 200 similar to the waveguide region 200 in FIG. 8, except that in FIG. 9, the conductive layer 29 above the dielectric, layer 28 extends proximate to the sample holding portion 23. In FIG. 9, the conductive layer 29' under the dielectric, layer 27 is in contact with the dielectric layer 27. The light 8 reflects from the conductive layers 29' under the dielectric layer 27 and from the conductive layers 29 above the dielectric layer 28.

Figure 10:
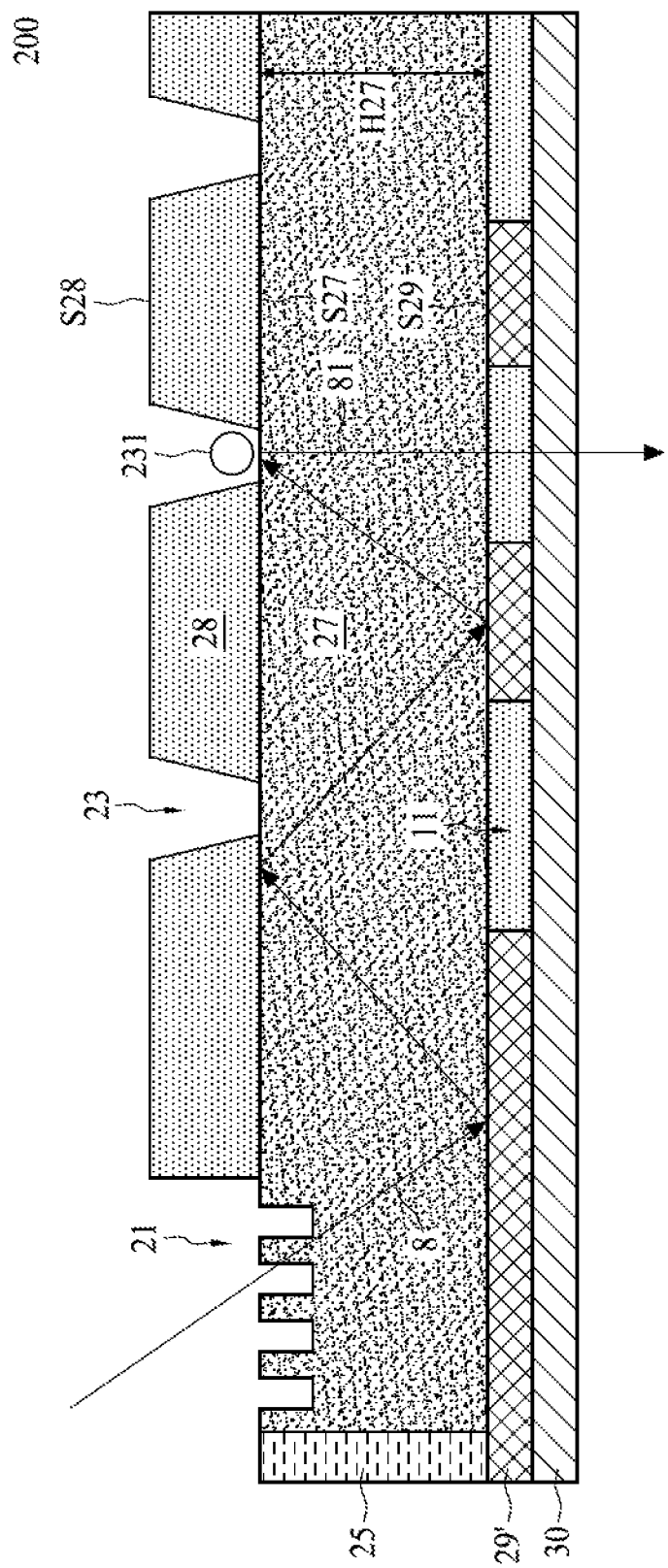

FIG. 10 illustrates a cross-sectional view of a waveguide region 200 similar to the waveguide region 200 in FIG. 9, except that in FIG. 10, a surface S28 of the dielectric layer 28 is exposed to an ambient environment. In some embodiments, a total area of the surface S28 is substantially equal to a total area of the interface S27. In some embodiments, a total area of the surface S29 of the conductive layer 29' is substantially less than the interface S27.

Figure 11:
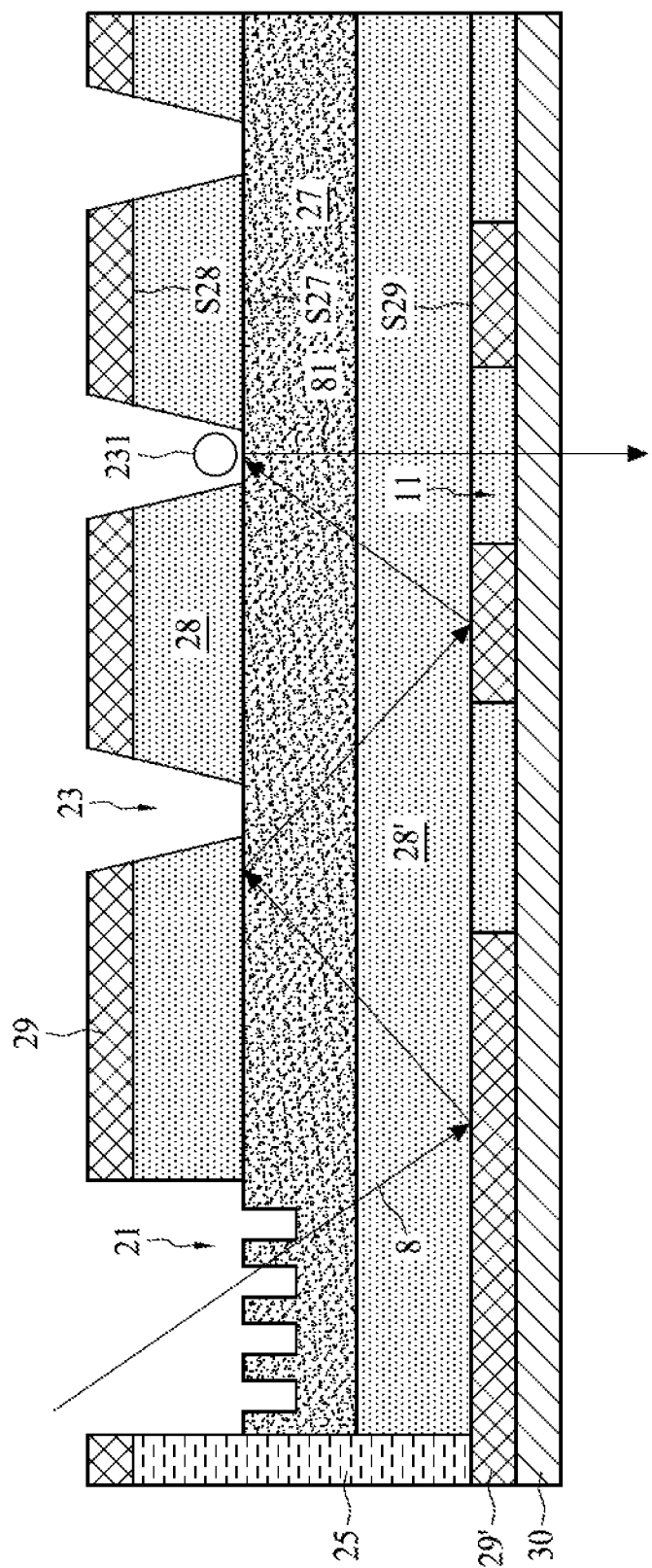

FIG. 11 illustrates a cross-sectional view of a waveguide region 200 similar to the waveguide region 200 in FIG. 8, except that in FIG. 11, the conductive layer 29 covers on top of the surface S28 of the dielectric layer 28. The conductive layer 29 covering the dielectric layer 28 extends proximate to the sample holding portion 23. A top portion of the recess of the sample holding portion 23 is surrounded by the conductive layer 29.

Figure 12:
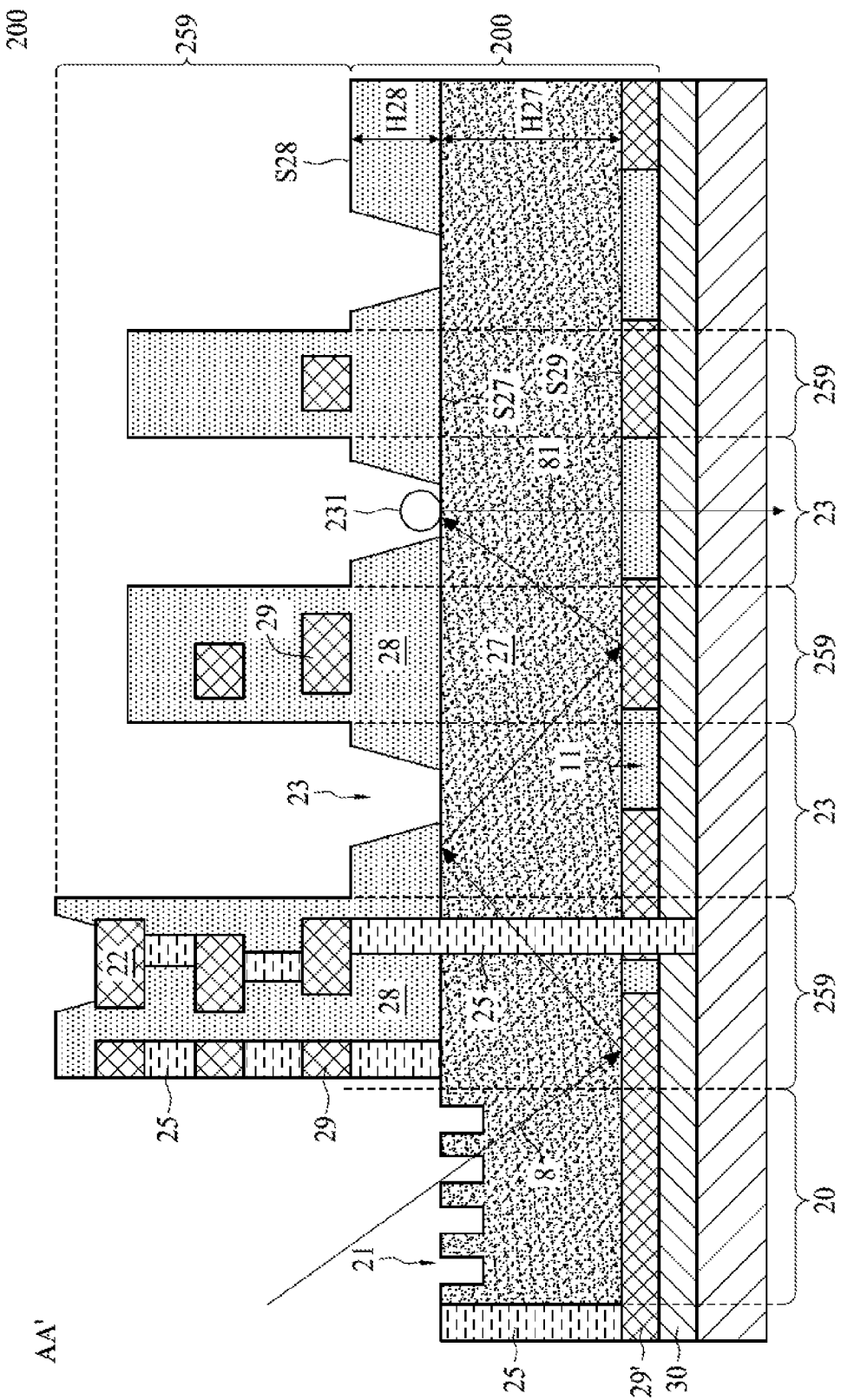

FIG. 12 illustrates a cross-sectional view of a waveguide region 200 from the cross-sectional line AA' in FIG. 1. FIG. 12 illustrates a cross-sectional view of a waveguide region 200 similar to the waveguide region 200 in FIG. 10, except that in FIG. 12, the waveguide region 200 includes a multilayer structure 259. The multilayer structure 259 is over the dielectric layer 28 except at where the sample holding portion 23 is disposed, and where the grating structure 21 is disposed. The multilayer structure 259 is partially covering the dielectric layer 28 such that the sample holding portion 23 and the grating of the grating structure 21 are exposed to an ambient environment.

The multilayer structure 259 includes the dielectric layer 28, the dielectric layer 27, the via structure 25, and the conductive layer 29. The via structure 25 and the conductive layer 29 are stacking on one another alternately in the multilayer structure 259 above the dielectric layer 28.

Proximate to a top of the multilayer structure 259 is a pad 22. The pad 22 is electrically connected to the conductive layer 29' below the dielectric layer 27. The pad 22 is connected through the via structure 25 and the conductive layer 29 in the multilayer structure 259 and through the via structure 25 passing through the dielectric layer 27. The pad 22 is between the grating structure 21 and the sample holding portion 23. A recess is above the pad 22 for other devices to connect with the pad 22.

In some embodiments, the multilayer structure 259 is an interconnect portion for the circuitry to transfer electric signals. The multilayer structure 259, between the grating structure 21 and the sample holding portion 23, includes the via structure 25 extending from the surface S28 of the dielectric layer 28, through the dielectric layer 28, through the dielectric layer 27, through the conductive layer 29', and through the filter layer 30. The multilayer structure 259 includes the dielectric layer 28, the via structure 25, the conductive layer 29, the dielectric layer 27, the conductive layer 29', or the filter layer 30 from top to bottom. The multilayer structure 259 includes the via structure 25 surrounded by the dielectric layer 27, the dielectric layer 28, the conductive layer 29', or the filter layer 30. The multilayer structure 259 includes the dielectric layer 28 on top of the dielectric layer 27. In some embodiments, the via structures 25 and the conductive, layer 29 in the multilayer structure 259 and bordering with the wave insert portion 20 are concurrently formed. The wave insert portion 20 includes a first boundary and a second boundary. The first boundary is at the left end of the wave insert portion 20. The second boundary is at the right end of the wave insert portion 20, or alternatively stated, between the wave insert portion 20 and the sample holding portion 23 and positioned in the dielectric layer 28. As shown in FIG. 12, the via structure 25 aligned to the first boundary of the wave insert portion 20 and positioned in the dielectric layer 27 is a first reflective structure. A second reflective structure is aligned to the second boundary and positioned over the dielectric layer 27. In some embodiments, the second reflective structure includes an alternating stack of the via structures 25 and the conductive layers 29. The first reflective structure and the second reflective structure serve to block light 8 and to reflect light 8 toward the grating structure 21. Note the reflective structure is designed to reflect the inserting light 8 and collect the maximum light intensity thereof into the dielectric layer 27. In some embodiments, the reflective structure can be a metal layer electrically isolated from other metals in the waveguide region 200 or outside of the waveguide region 200.

Figure 13:
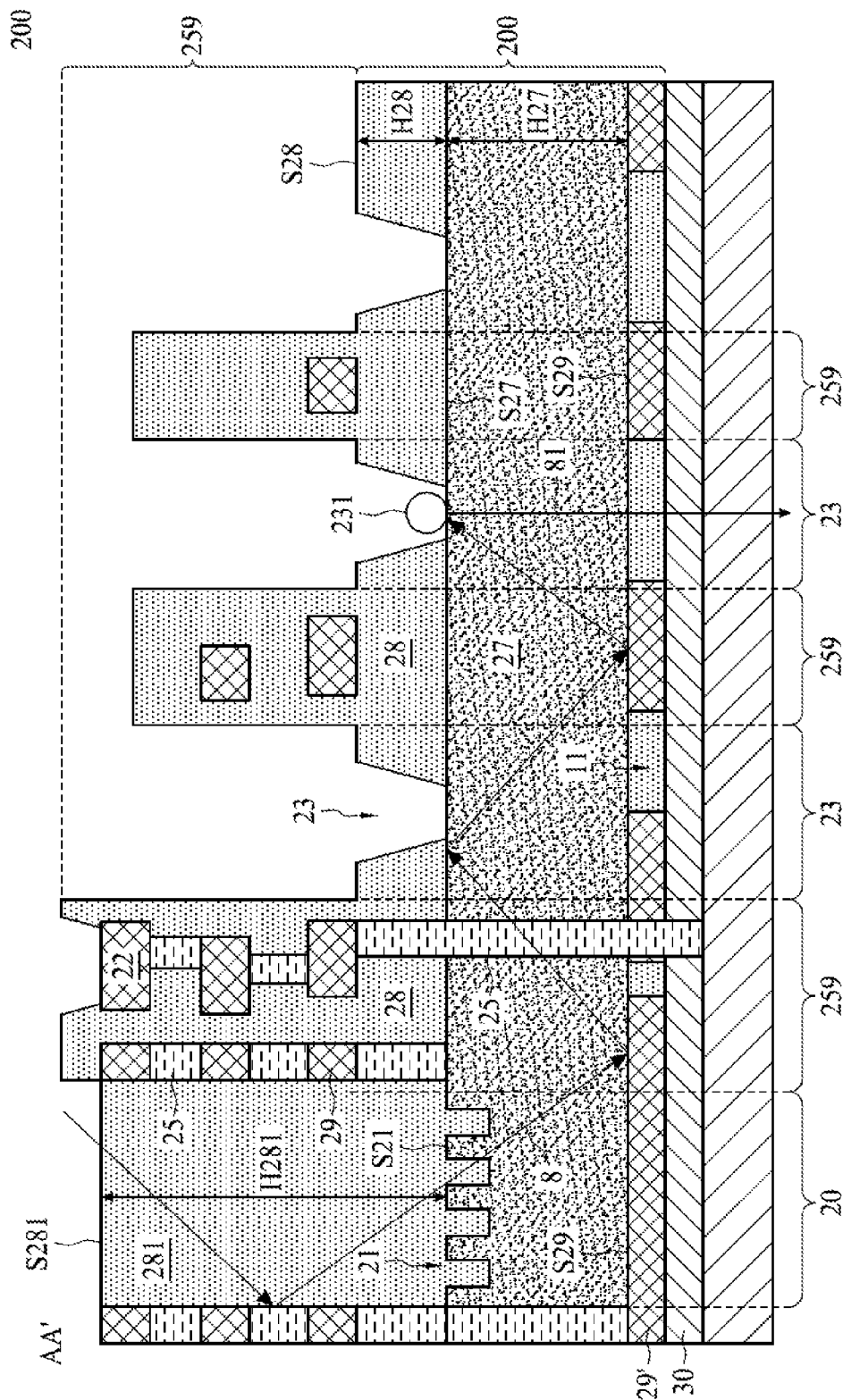

FIG. 13 illustrates a cross-sectional view of a waveguide region 200 from the cross-sectional line AA in FIG. 1. In FIG. 13, an wave insert portion 20 of the waveguide region 200 includes a dielectric column 281 covering on top of the grating of the grating structure 21.

A light 8 incident upon the wave insert portion 20 is guided through the dielectric column 281 toward the grating of the grating structure 21. The light 8 is reflected from the via structure 25 or the conductive layer 29 adjacent to the dielectric, column 281. The via structure 25 and the conductive layer surrounding the dielectric column 281 confines the light 8 inside the dielectric column 281. A lower portion of the dielectric column. 281 is inside a groove of the grating near the grating structure 21. The wave insert portion 20 includes the dielectric column 281 over the dielectric, layer 27. In some embodiments, the height H281 is substantially smaller than the thickness H28. In some embodiments, the conductive layers 29 in the multilayer structure 259 are formed concurrently with the conductive layers 29 at the boundary of the wave insert portion 20. In some embodiments, the conductive layers 29 in the multilayer structure 259 are electrically connected to the light sensing region under the waveguide region 200. In some embodiments, the conductive layers 29 under the dielectric layer 27 are not, electrically connected to the light sensing region.

Figure 14:
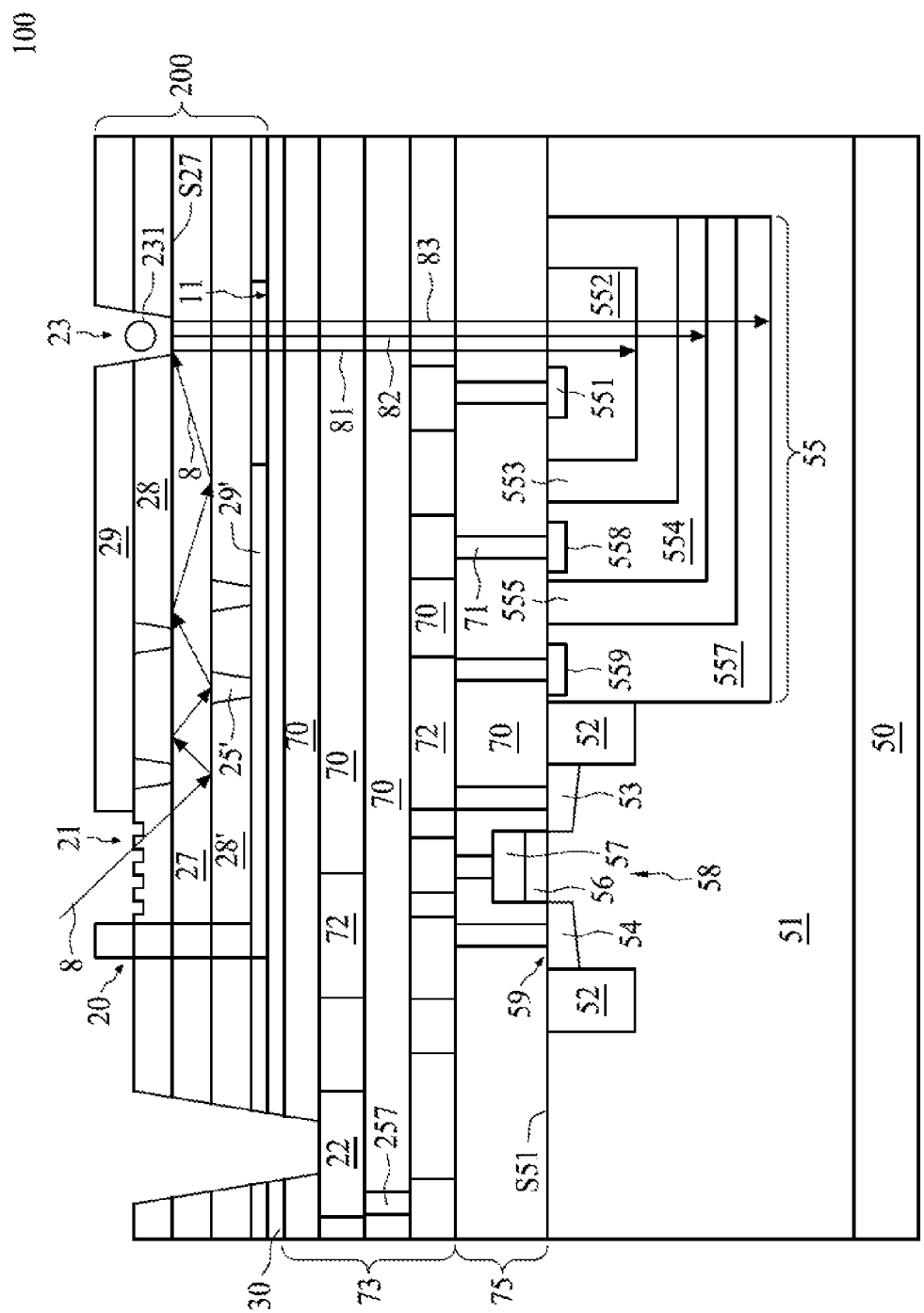
FIGS. 14 to 16 are cross-sectional views of a semiconductive device, in accordance with some embodiments of the present disclosure.

FIG. 14 illustrates a semiconductive device 100 including an interconnect region 73, a waveguide region 200, and a light sensing region 55. In some embodiments, the waveguide region 200 is above the interconnect region 73 and/or the light sensing region 55. The interconnect region 73 is between the waveguide region 200 and the light sensing region 55. The light sensing region 55 is under the waveguide region 200 and below the interconnect region 73. The light sensing region 55 is in an epitaxy region 51. The light sensing region 55 is above the semiconductive substrate 50.

A light 8 incident is upon the grating of the grating structure 21 at the wave insert portion 20. The light 8 travels from the wave insert portion 20 to the waveguide portion 278. The light 8 is mostly confined within the dielectric layer 27. The light 8 reaches the sample holding portion 23 of the waveguide region 200 and illuminates on the specimen 231 to be examined. In response to the light 8, the specimen 231 emits a light of a certain wavelength. The wavelength of the emitted light is characteristic of a material in the specimen 231. For example, in some embodiments, the specimen 231 emits different wavelengths of a light 81, a light 82, and a light 83. The light 81, the light 82, and the light 83 pass through the aperture 11 near the bottom of the waveguide region 200. The light 81, 82, and 83 travels through the filter layer 30 between the waveguide region 200 and the interconnect region 73.

In some embodiments, the filter layer 30 is a laser beam filter. The filter layer 30 removes scatter and aberrations in light 8 and a beam of a light containing the light 81, 82, and 83. The filter layer 30 attenuates a phase and/or intensity of the beam of the light containing the light 81, 82, and 83 such that some noises of side fringes or spatially varying intensity of the beam are modified. The lights 81, 82, 83 pass though the dielectric, layer 70 and enter into the light sensing region 55.

In the light sensing region 55, the lights 81, 82, and 83 are absorbed at different regions 552, 554, 557 respectively. Specifically, the lights 81, 83 are absorbed at junctions between regions 552/553, regions 554/555, and regions 557/51. In some embodiments, region 557 is referred to as a deep well region 557. In some embodiments, region 554 is referred to as a middle well region 554, and region 552 is referred to as a shallow well region 552. A quantum efficiency of each region 552, 554, 557 is different for different wavelengths of light. For example, the quantum efficiency of region 552 is larger for a wavelength of the light 81 than for another wavelength of a light, such as the wavelength of the light 82 or 83. The quantum efficiency of region 554 is larger for the wavelength of the light 82 than for another wavelength of a light, such as the wavelength of the light 81 or 83. The quantum efficiency of region 557 is larger for the wavelength of the light 83 than for another wavelength of a light, such as the wavelength of the light 81 or 82. Most of the light 81 is stopped and absorbed in region 552. Most of the light 82 passes through region 552 toward region 554. Most of the light 82 is stopped and absorbed in region 554. Most of the light 83 passes through region 552 and region 554 toward region 557. Most of the light 83 is stopped and absorbed in region 557.

The light 81 absorbed in region 552 converts to charge carriers in region 552. In some embodiments, the charge carrier can be positive or negative. The charge carriers flow to heavily doped region 551, 559 or 558 in order to transfer information about the specimen 231 to the circuitry in the interconnect region 73 for further processing and/or output. The light 8 is converted by a photo-sensitive element in region 552, 554, or 557 into data information.

The charge carrier is transferred through heavily doped regions 551, 558, 559 in each region 552, 554, and 557' respectively, to a first layer via 71. The first layer via in some embodiments may also function as a contact. For example, the charge carriers are transferred from region 552 to a heavily doped region 551 within region 552. In some embodiments, the heavily doped region 551 and region 552 include a same type of dopant, such as a positive-type or a negative-type of dopant. The charge carriers are transferred from region 554 to the heavily doped region 558 within region 554. In some embodiments, region 554 and heavily doped region 558 include a same type of dopant. The charge carriers are transferred from region 557 to a heavily doped region 559 within region 557. In some embodiments, the heavily doped region 559 and region 557 include a same type of dopant.

In some embodiments, region 552, 554, or 557 is connected to another semiconductive device, such as a transistor 59, through a heavily doped region 551, 558, or 559. In some embodiments, the heavily doped region 551, 558, or 559 is connected to some other semiconductive device, such as the transistor 59, through the contact 71 or a metal line 72. Data information is transferred from the transistor 59 to the circuitry in the interconnect region 73. In some embodiments, the pad 22 is composed of conductive material. The pad 22 is electrically connected to the transistor 59 through the via structure and/or the interconnects. In some embodiments, multiple transistors 59 are connected to multiple light sensing regions 55 in order to transfer various data information about the specimens 231 in multiple sample holding portions 23.

The transistor 59 is connected to the photo-sensitive element in the light sensing region 55 in order to transfer image data to the circuitry for further processing and/or output. In some embodiments, the photo-sensitive element includes a photosensitive, diode.

In some embodiments, the transistor 59 is a transfer transistor for transferring the image data captured by a corresponding photo-sensitive element to external circuitry. In some embodiments, additional transistors with various functions are also included in the semiconductive device 100. For example, a reset transistor, a source follower transistor, and/or a select transistor are included in the semiconductive substrate 50. In some embodiments, other transistors in the semiconductive device 100 are structured similarly to the transistor 59.

In some embodiments, the dielectric layer 70 includes a refractive index greater than or equal to the first refractive index of the dielectric layer 27 or the second refractive index of the dielectric layer 28. In some embodiments, in FIG. 14, some via structures 25, 25' and some dummy conductive layers 29 and 29' are composed of a material similar to a material in the interconnects, such as aluminum, copper, titanium nitride, tungsten, titanium, tantalum, tantalum nitride, nickel silicide, cobalt silicide, TaC, TaSiN, TaCN, TiAl, TiAlN, other suitable metals, and/or combinations thereof. The via structure 25, 25' and the dummy conductive layers 29, 29' serves to constrain migrating direction of light 8 in the waveguide region 200. The dummy conductive layers 29, 29' may also be metal layers. In some embodiments, the via structure 25, 25' and the dummy conductive layers 29, 29' are in the dielectric layer 28 in the waveguide region 200. In some embodiments, the via structure 25, 25' or the dummy conductive layers 29, 29' serves to block light and can be electrically disconnected to the interconnect region 73 or other conductors within or outside of the waveguide region 200. Since, the via structure 25, 25' of the aforesaid is not electrically connected to the interconnect region 73, said via structure may functionally be referred to as a reflective, structure. However, the reflective structure used in the present disclosure encompasses the (1) via structure 25, 25' electrically connected to the interconnect region 73 or other conductors within or outside of the waveguide region 200, and (2) via structure 25, 25' not electrically connected to the interconnect region 73 or other conductors within or outside of the waveguide region 200.

The light sensing region 55 is a multi-junction photodiode for detecting light of various wavelengths. In some embodiments, the semiconductive substrate 50 includes first conductive type dopants, such as some positive-type dopants. The epitaxy region 51 includes the first conductive type dopants. Region 557 includes second conductive type dopants such as negative-type dopants. Region 555 includes the first conductive type dopants. In some embodiments, region 555 is a well region 555. Region 554 includes the second conductive type dopants. Region 553 includes the first conductive type dopants. In some embodiments, region 553 is a well region 553. Region 552 includes the second conductive type dopants. The heavily doped region 551, 558, or 559 includes the second conductive type dopants.

The semiconductive substrate 50 is a silicon substrate or another semiconductor substrate including the first conductive type dopants in a certain concentration. The first conductive type dopants, such as a positive conductive, type dopants, are in the semiconductive substrate 50. For example, the semiconductive substrate 50 includes a predetermined doping concentration of boron. In some embodiments, the epitaxy region 51 is a lightly doped silicon epitaxy such that a doping concentration of the first conductive, type dopants in the epitaxy region 51 is less than the predetermined doping concentration in the semiconductive substrate 50. Region 557, 554, or 552 includes the second conductive type dopants, such as phosphorus, in some predetermined doping concentrations. In some embodiments, the predetermined doping concentrations of the second conductive type dopants in region 557, 554, and 552 are substantially the same. Region 555 or 553 include the first conductive type dopants, such as boron, in some predetermined doping concentrations. In some embodiments, the predetermined doping concentrations of the first conductive type dopants in regions 555 and 553 are substantially the same.

In some embodiments, a portion of region 557, 554, or 552 closer to the surface S51 includes a higher doping concentration than another portion of region 557, 554, or 552 respectively. The portion of region 557, 554, or 552 closer to the heavily doped region 559, 558, or 551 serves as a terminal of region 557, 554, or 552 for an outer connection. In some embodiments, the heavily doped region 559, 558, or 551 includes a material, such as a metal or other conductive materials.

The epitaxy region 51 includes, near the surface S51, isolation regions 52. In some embodiments, the isolation region 52 is a shallow trench isolation (STI) feature or a local oxidation of silicon (LOCOS) feature. The isolation regions 52 define and isolate various elements or regions from each other in the epitaxy region 51 or in the semiconductive substrate 50. For example, the isolation regions 52 isolate adjacent light sensing region 55 from each other, isolate the light sensing region 55 from the transistor 59, or isolate some components of the circuitry from each other, etc. In some embodiments, the isolation region 52 is made of a dielectric material.

The transistor 59 is disposed at the surface S51 of the epitaxy region 51. The transistor 59 includes a gate structure 58 and a source region 53 and a drain region 54. The gate structure 58 includes a gate dielectric 56 and a gate electrode 57.

The gate dielectric 56 is composed of a high-k dielectric layer or combination thereof. The gate dielectric 56 is made of any suitable dielectric material, such as hafnium oxide ($HfO_2$), hafnium silicon oxide (HfSiO), transition metal-oxides, oxynitrides of metals, metal aluminates, other suitable dielectric materials, and/or combinations thereof. In me embodiments, the gate dielectric 56 includes an interfacial layer between the gate dielectric 56 and the epitaxy region 51 in order to reduce damages between the gate dielectric 56 and the epitaxy region 51.

The gate structure 58 the source region 53, and the drain region 54 of the transistor 59 are connected to a plurality of first layer via, or hereinafter referred to as "contacts" 71. The contacts 71 pass through the dielectric layer 70 such that the contacts 71 connect with some portions of the gate structure 58, the source region 53, or the drain region 54. The contacts 71 are in contact with a portion of the surface S51 above the source region 53, the drain region 54, or the light sensing region 55. In some embodiments, the contacts 71 and the dielectric layer 70 are in an inter-layer dielectric (ILD) layer 75; the ILD layer 75 is above the transistors 59 and the light sensing region 55; the transistor 59 is proximate to the light sensing region 55; the interconnect region 73 includes the transistor 59, the ILD layer 75, the dielectric layer 70, and metal lines 72. For brevity, the via structure and the metal lines are generalized as interconnects in the present disclosure.

Figure 15:
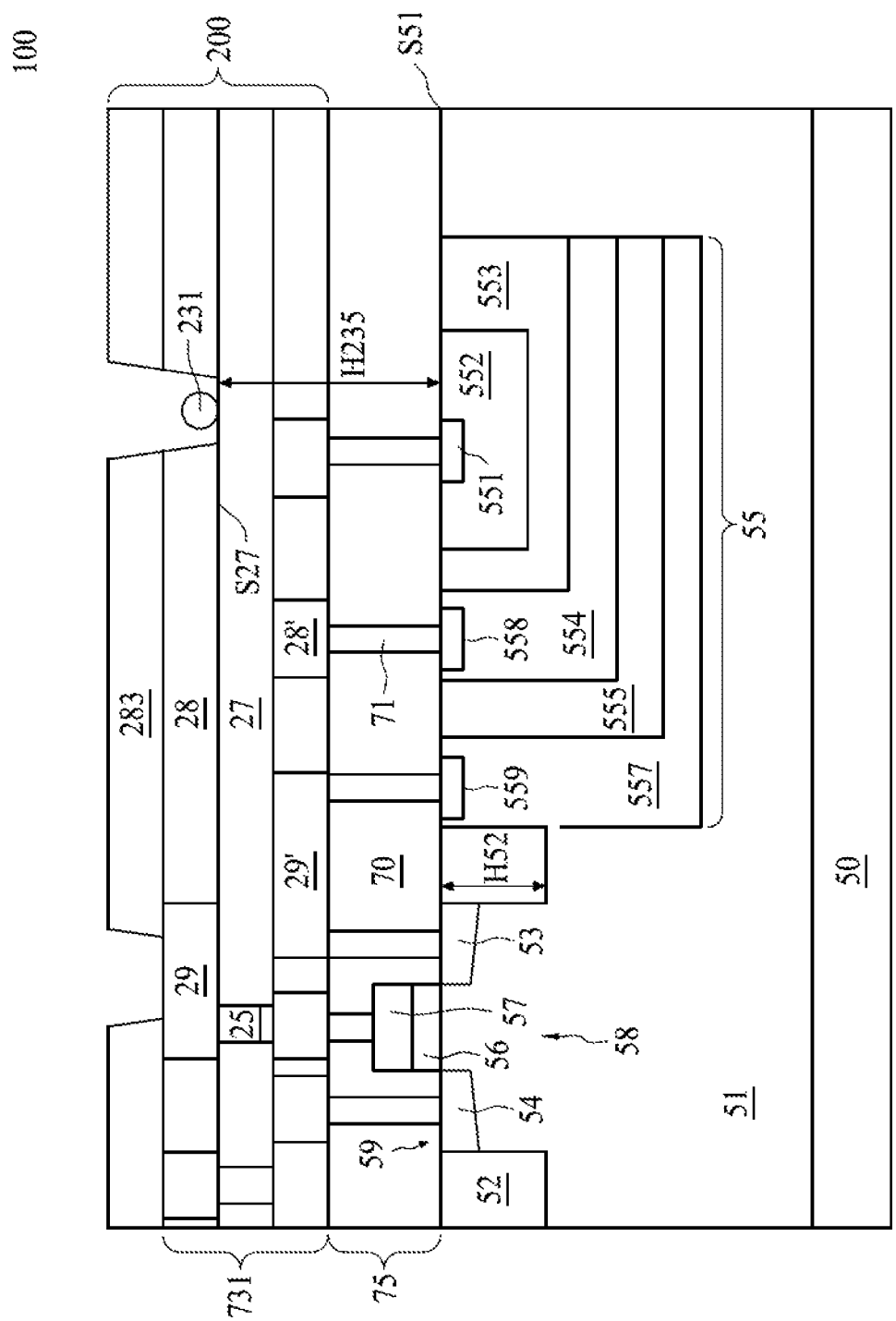

In FIG. 14, the dummy conductive layers 29, 29' or the via structures 25, 25' include similar shape as to the conductive layer 29, 29' or the via structure 25, 25' in FIG. 15. However, in FIG. 14, the dummy conductive layers 29, 29' or the via structures 25, 25' are not electrically connected with other conductors. While in FIG. 15, the conductive layer 29, 29' or the via structure 25, 25 are electrically connected with other conductors. The "other conductors" referred herein include the conductive routes electrically connected to the light sensing region 55.

In FIG. 15, waveguide region 200 includes the conductive layer 29' in the dielectric, layer 28', the via structure 25 in the dielectric layer 27, and the conductive layer 29 in the dielectric layer 28. A bottom of the sample holding portion 23 is approximately at the interface S27.

The conductive layer 29', the via structure 25, and the conductive layer 29 are in an interconnect region 731. The interconnect region 731 is in the waveguide region 200. The waveguide region 200 includes dielectric layer 28, dielectric layer 28', and dielectric layer 27 in contact with components such as conductive layer 29, the via structure 25, and the conductive, layer 29' in the interconnect region 731. The interconnect region 731 is referred to as a first interconnect portion capable of transmitting electrical signal from the light sensing region 55 to other external circuits. The multilayer structure 259 in FIG. 12 is referred to as a second interconnect portion electrically connected With light sensing region 55 under the waveguide region 200.

The conductive layer 29' in the first interconnect portion is electrically connected with the light sensing region 55. The conductive layer 29' can be in a first metal layer closest to the light sensing region 55. The conductive layer 29 can be a second metal layer. The conductive layer 29' is electrically connected to vias 71 in ILD layer 75. The first interconnect portion is positioned in the waveguide region 200 such that height H235 is reduced. Thus, attenuation of light from sample 231 is minimized before reaching light sensing region 55.

Figure 16:
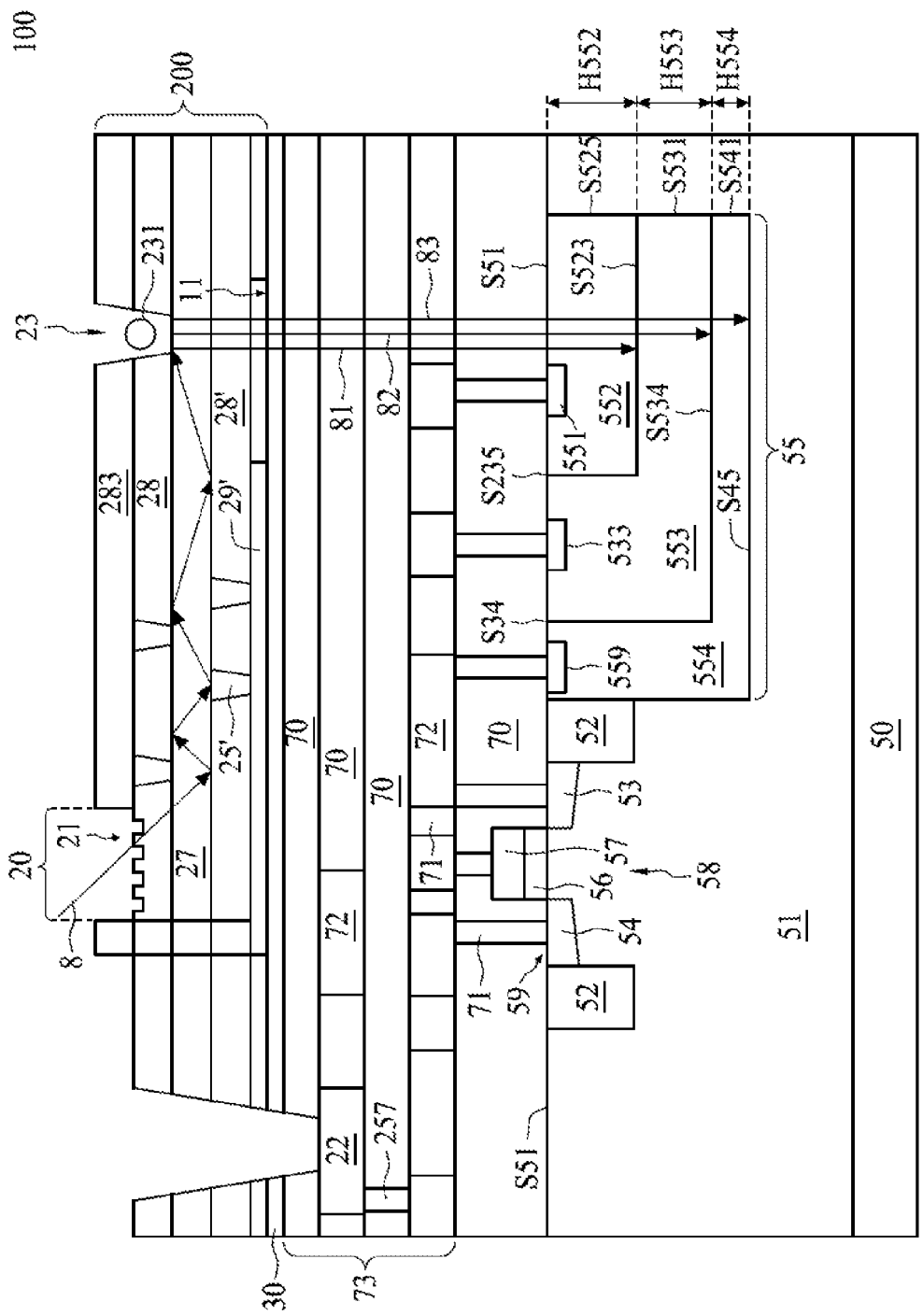

FIG. 16 is similar to FIG. 14, except that some components such as a top layer of a waveguide region 200, a layer below the dielectric layer 27, regions in light sensing region 55, and a first layer via 71 are different. The differences are briefly discussed below.

The top layer of the waveguide region 200 in FIG. 14 is a conductive layer 29. The top layer of the waveguide region 200 in FIG. 16 is a passivation layer 283. In some embodiments, the passivation layer 283 includes dielectric material, such as a dielectric material in the dielectric layer 28. In some other embodiments, the passivation layer 283 is composed of material having a refractive index lower than the second refractive index of the dielectric layer 28 or the first refractive index of the dielectric layer 27. A top portion of the recess of the sample holding portion 23 is in the passivation layer 283. A bottom portion of the recess is in the dielectric layer 28. The passivation layer 283 is on top of the dielectric layer 28. The passivation layer 283 covers the dielectric layer 28 up to a wave insert portion 20 such that the grating structure 21 is exposed.

The layer below the dielectric layer 27 in FIG. 16 is the dielectric layer 28'. The dielectric layer 28' is a first cladding layer. The dielectric 28 above the dielectric layer 27 is a second cladding layer. The dielectric layer 27 is a core layer. In some embodiments, the dielectric layer 28, 28' are composed of material having a refractive index lower than the first refractive index of the dielectric layer 27. In some embodiments, a refractive index mostly increases in a direction of a propagation of the light 81, 82, or 83. For example, the refractive index of the dielectric layer 70 is higher than the refractive index of the dielectric layer the second refractive index of the dielectric layer 28 is higher than the refractive index of the passivation layer 283.

In FIG. 14, the regions in the light sensing region 55 include three regions 552, 554, and 557 composed of the second conductive type dopants and two regions 553 and 555 composed of the first conductive type dopants. In FIG. 16, the regions in the light sensing region 55 include two regions 552 and 554 composed of the second conductive type dopants and one region 553 composed of the first conductive type dopants. The detailed light sensing region 55 in FIG. 16 is discussed below.

An interface between a region composed of the first conductive type dopants and another region composed of the second conductive type dopants is a p-n junction. Each interface at different locations, with different lengths, or with different orientations is capable of detecting different wavelengths of the light 81, 82, or 83 distinctively. Different combinations of p-n junction serve as different photodiodes capable of detecting different wavelengths of the light 81, 82, or 83. For example, an interface S45 between region 554 and the epitaxy region 51 is a p-n junction. The interface S525 is oriented vertically or is substantially orthogonal to the surface S51. The interface S525 is suitable for detecting a wavelength of the light 81 or some wavelength of light shorter than the wavelength of the light 81. In some embodiments, region 553 of first conductive type is surrounded by regions 552 and 554 of the second conductive type. The interface S34 is oriented laterally. The interface S34 is a p-n junction with a length substantially equal to a sum of height H552 and H553. The interface S34 is suitable for detecting the light 82 or some lights with a shorter wavelength than the wavelength of the light 82.

In FIG. 14, heavily doped regions 551, 558, and 559 include the second conductive type dopants. Regions 552, 554, and 557 also contain the second conductive type dopants. In FIG. 16, the heavily doped region 533 includes the first conductive type dopants. Regions 553 also contains the first conductive type dopants. For example, in FIG. 16, region 552 contains negative conductive type dopants. Energy in the light 81 is absorbed in a depletion region of a p-n junction near the interface S523 or the interface S235 and the generated electron-hole pair is separated by the electric field. The negative carriers in region 552 flow through the heavily doped region 551 as a negative, current. The positive carriers in region 553 flow through the heavily doped region 533 as a positive current Region 553 contains positive conductive type dopants. Energy in the light 82 is absorbed in a depletion region of a p-n junction near the interface S534 or the interface S34 so as to separate positive and negative carriers. The negative carriers in region 554 flow through the heavily doped region 559 as a negative current. The positive carriers in region 553 flow through the heavily doped region 533 as a positive current.

Figure 17:
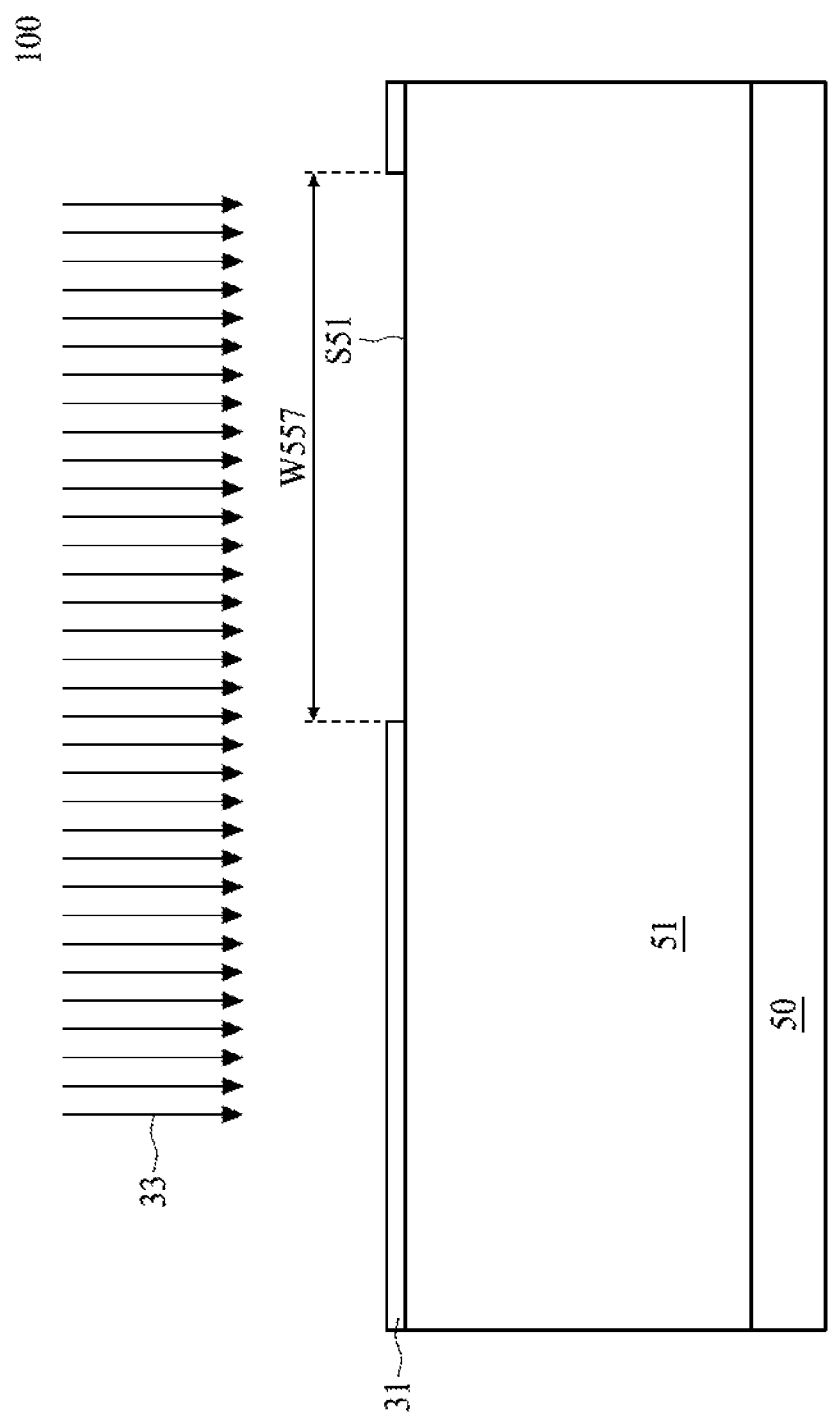
FIGS. 17 to 44 are cross-sectional views of an operation in a method for manufacturing a semiconductive device, in accordance with some embodiments of the present disclosure.

In FIG. 17, a semiconductor material, such as silicon germanium (SiGe) or silicon (Si), is epitaxially grown in the semiconductive substrate 50 to form the epitaxy region 51 by, for example, a selective epitaxial growth (SEG). In an embodiment, impurities are added to the epitaxy region 51 during a growth (e.g., in-situ doping). Exemplary dopants include arsenic, phosphorous, antimony, boron, boron difluoride, and/or other possible impurities. Sources for boron include diborane gas used during SiGe epitaxy. Boron doped in a SiGe is accomplished by introducing boron-containing gas, in an in-situ fashion, to an epitaxial SiGe growth. In some embodiments, boron or other dopants is formed by implantation operations such that the epitaxy region 51 includes a positive dopant.

A resist 31 is covering on top of the epitaxy region 51. Ion implantation 33 is performed over the epitaxy region 51. A resist 31 includes a pattern with a width W557 of an opening well exposing the epitaxy region 51 to ion implantation 33. In some embodiments, dopants of a negative-type are implanted into the epitaxy region 51 through high-energy collisions at an atomic level such that the dopants are below the surface S51.

Figure 18:
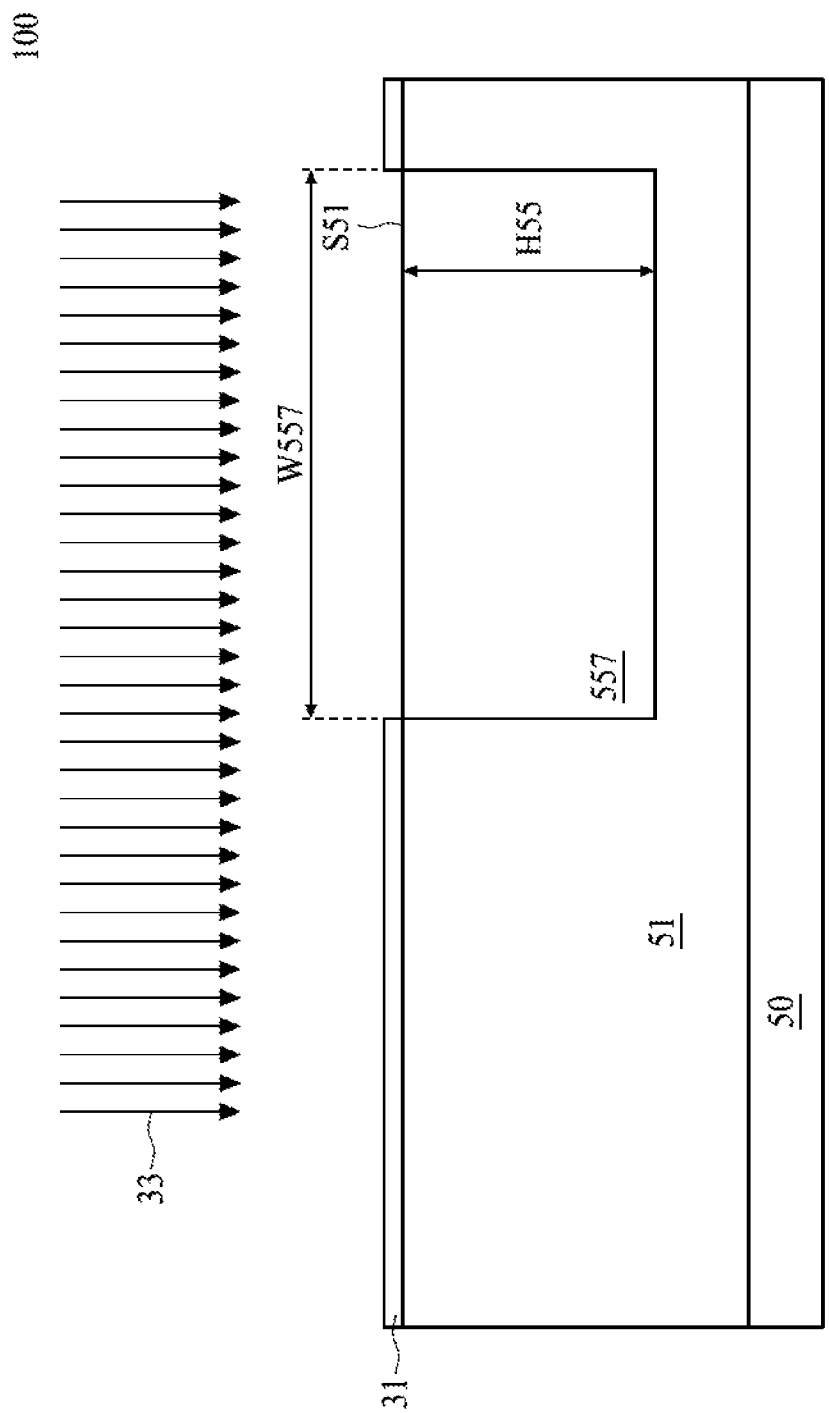

In FIG. 18, ion implantation 33, including a first predetermined energy, implants dopants into the epitaxy region 51 so as to form region 557 under the surface S51 by a depth substantially equal to the height H55. The resist 31 is stripped after region 557 is formed.

Figure 19:
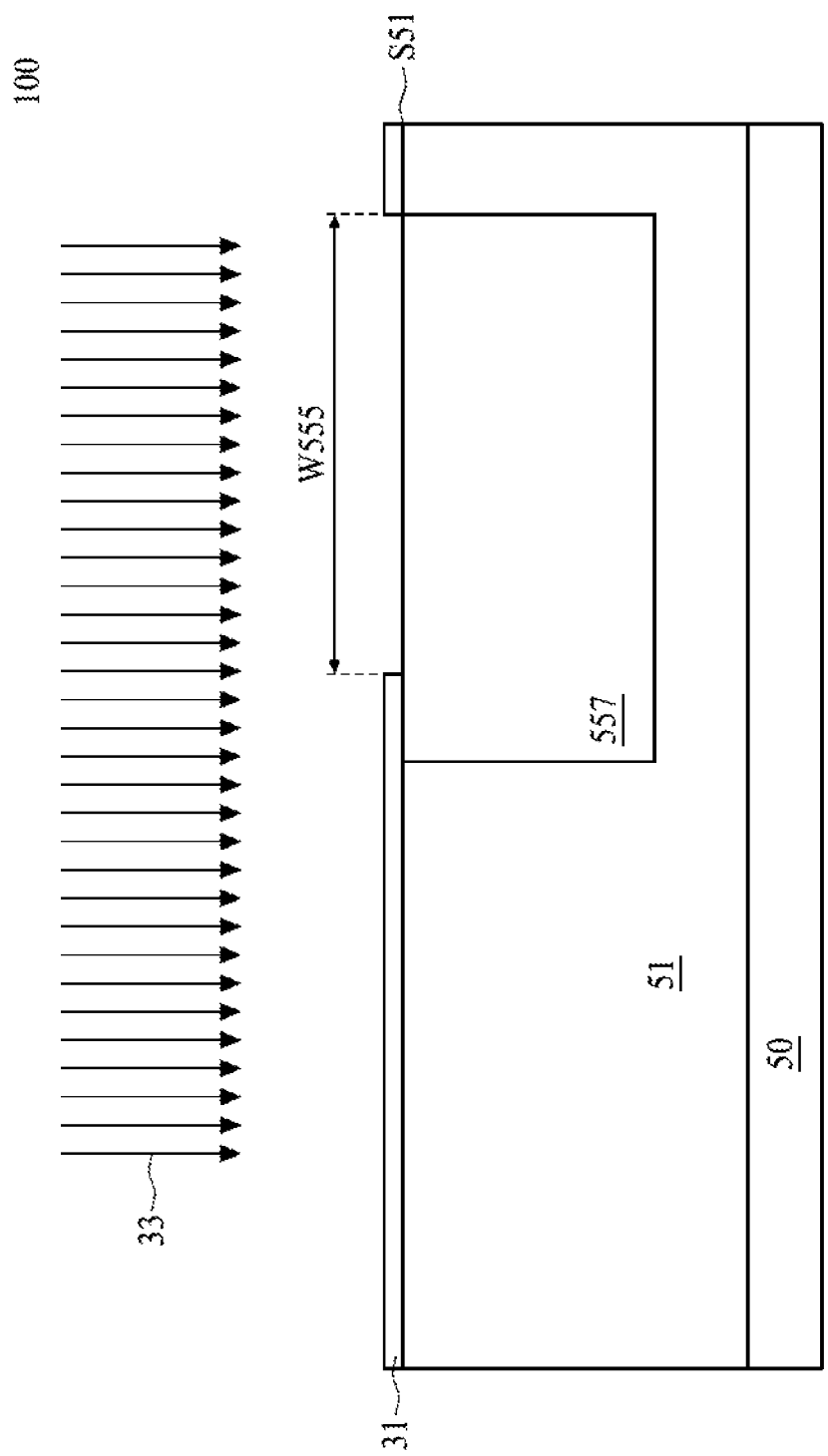

In FIG. 19, another resist 31 with a width W555 of an opening well is partially covering region 554. The opening well exposes region 557 to another ion implantation 33. In some embodiments, the width W555 is shorter than the width W557 for forming the region 557 shown in FIG. 18.

Figure 20:
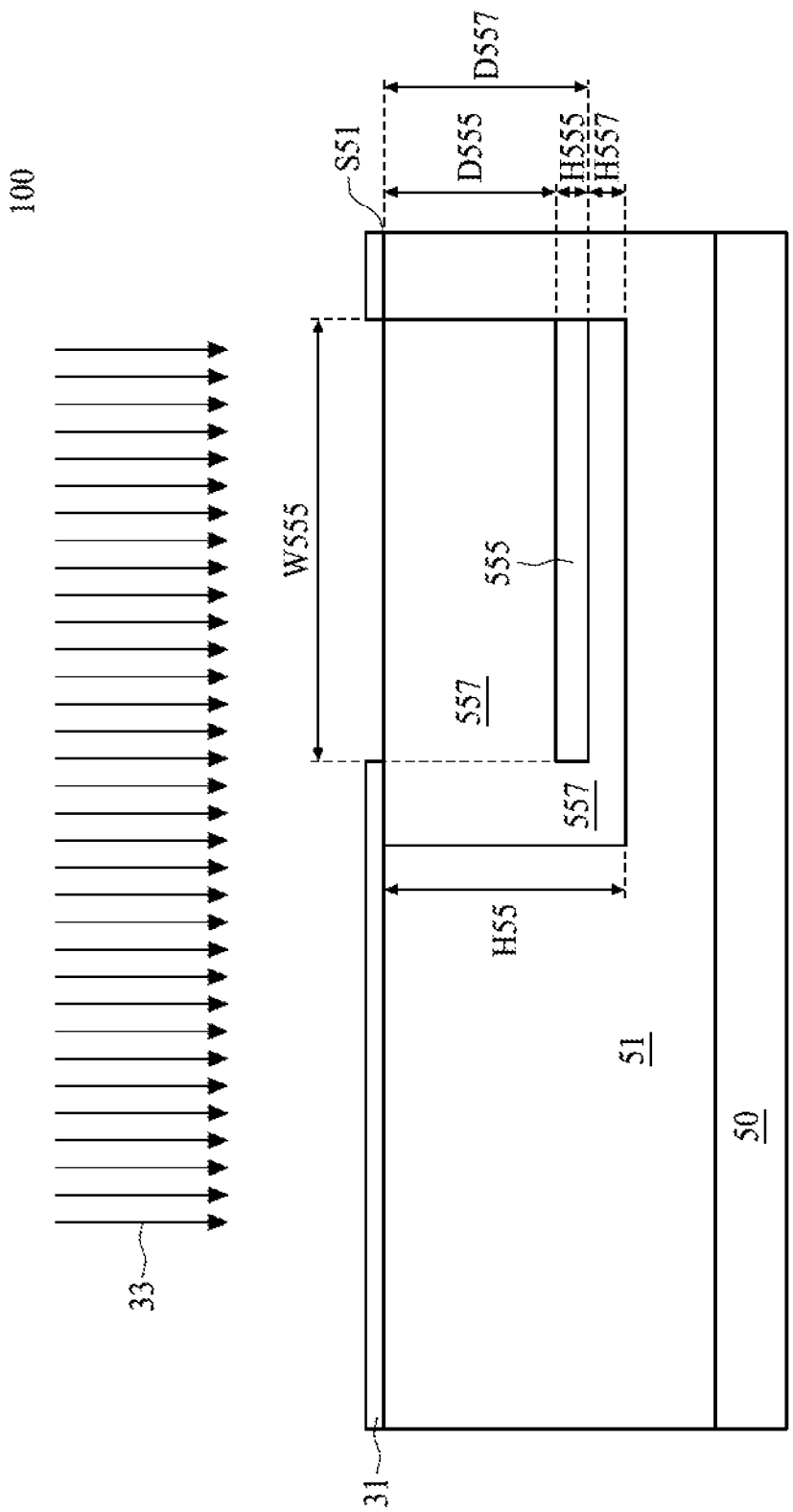

In FIG. 20, ion implantation 33, including a second predetermined energy, implants dopants into region 557 so as to form a horizontal portion of region 555 above region 557 by a height H557 and under the surface S51 by a depth D555. The second predetermined energy is adjusted to be smaller than the first energy such that dopants are implanted around a shallower region 555. In some embodiments, the dopants are of a same type as the epitaxy region 51, such as a positive-type. The resist 31 is stripped after region 555 is formed. Region 557 above and below region 555 includes the dopants, such as negative dopants, opposite to a conductive type of region 555.

Figure 21:
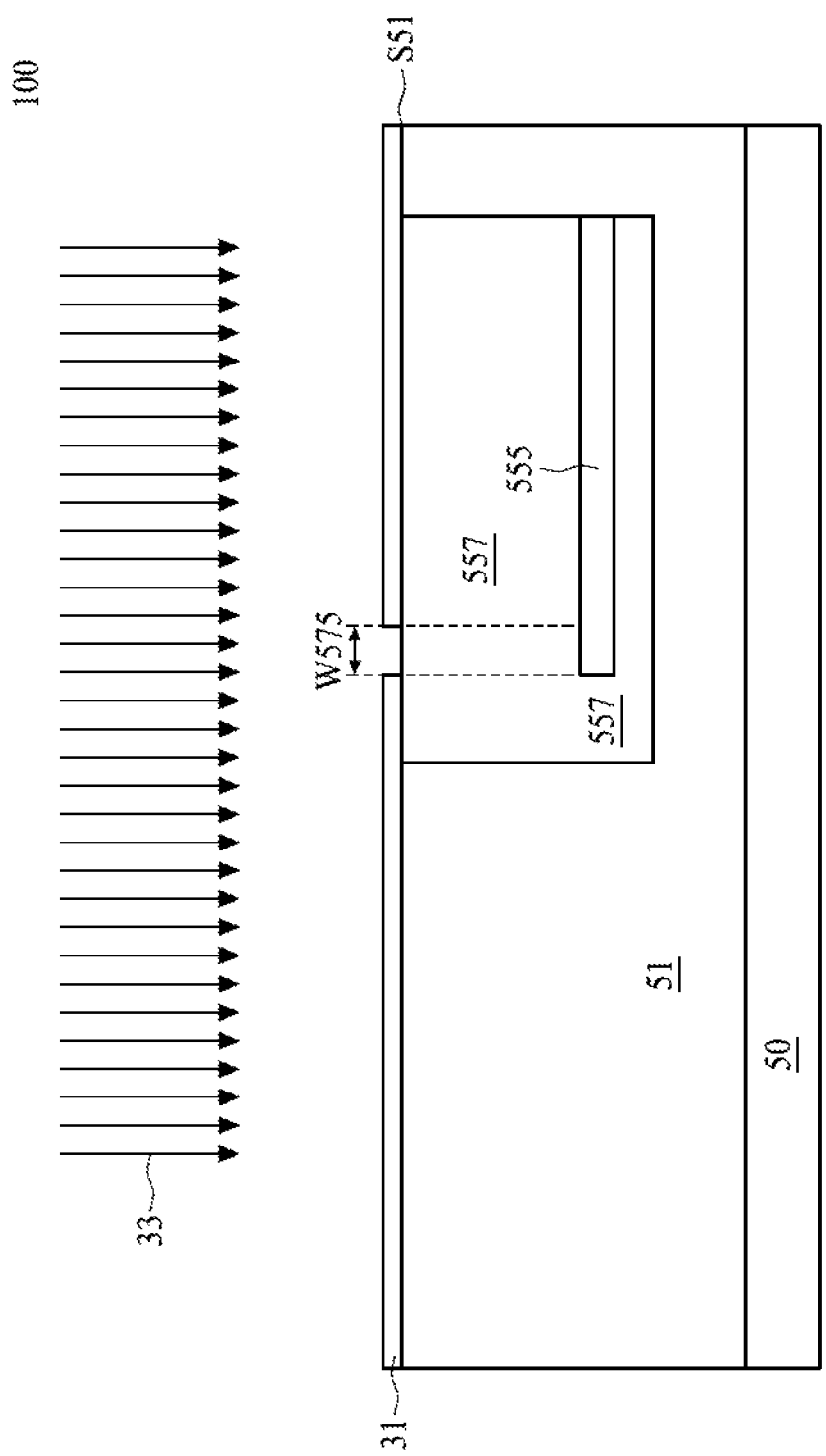

In FIG. 21, another resist 31 with a width W575 of an opening well is partially covering region 557. The opening well exposes region 557 to another ion implantation 33. The opening well is aligned to an end of region 555.

Figure 22:
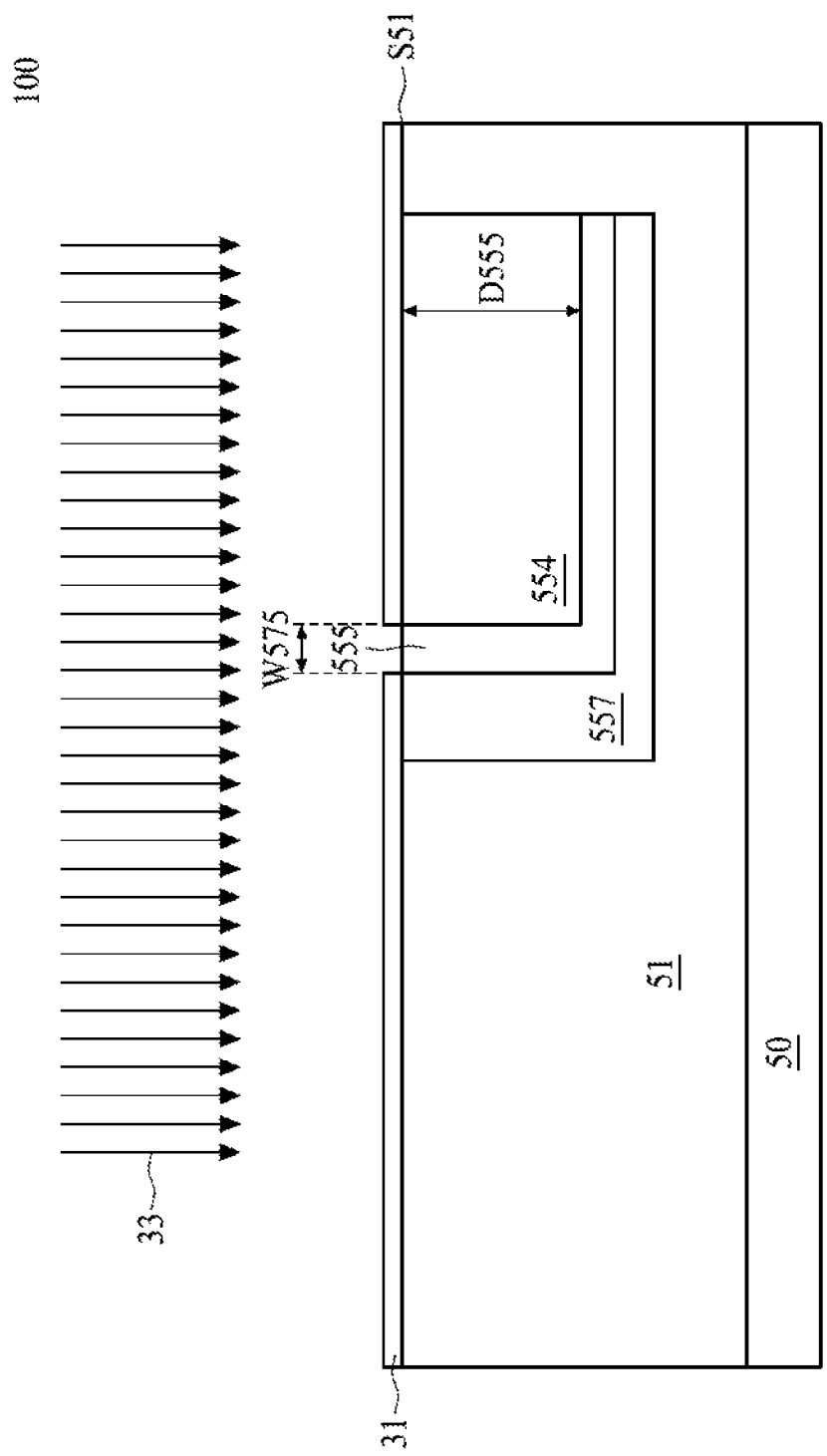

In FIG. 22, ion implantation 33, including a third predetermined energy, implants dopants into region 557 so as to form a lateral portion of region 555 above the horizontal portion of region 555. The lateral portion of region 555 includes a depth D555. The third predetermined energy is adjusted to be in a range smaller than the second energy such that dopants are implanted from the depth D555 up to the surface S51. In some embodiments, ion implantation 33 in FIG. 22 includes multiple operations of implantation with a variety of ion energies. In order to form a vertical implant region, different energies of ions are required to achieve said doping profile. In some embodiments, the dopants are of a same type as the horizontal portion of region 555 such as a positive-type. The resist 31 is stripped after the lateral portion of region 555 is formed. Region 554 above region 555 includes the dopants of an opposite conductive type to region 555, such as negative dopants.

Figure 23:
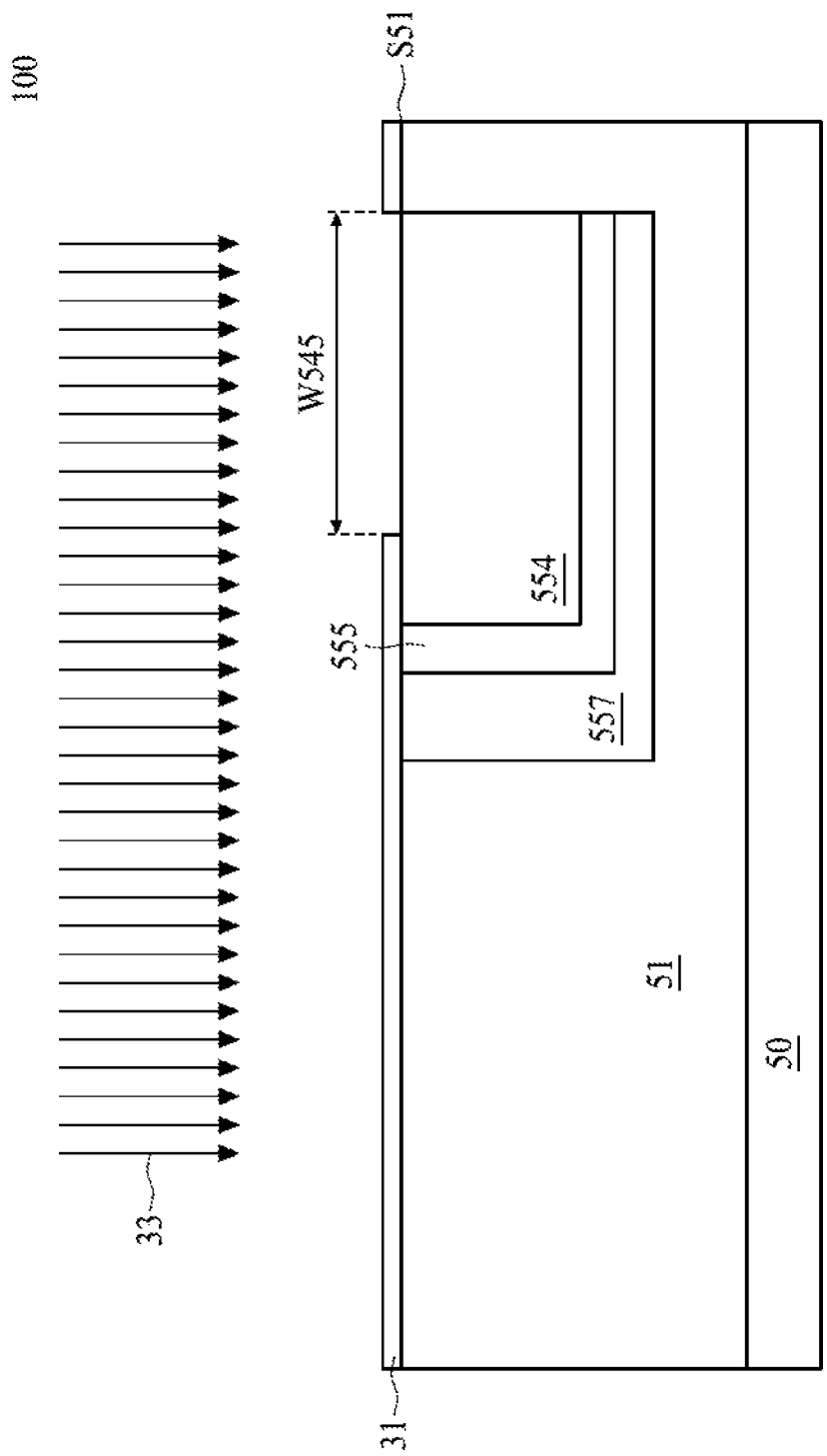

In FIG. 23, another resist 31 with a width W545 of an opening well is partially covering region 554. In some embodiments, the width W545 is shorter than the width W555 for forming the region 555 shown in FIG. 20. The opening well exposes region 554 to another ion implantation 33. The opening well is aligned to an end between region 554 and the epitaxy region 51.

Figure 24:
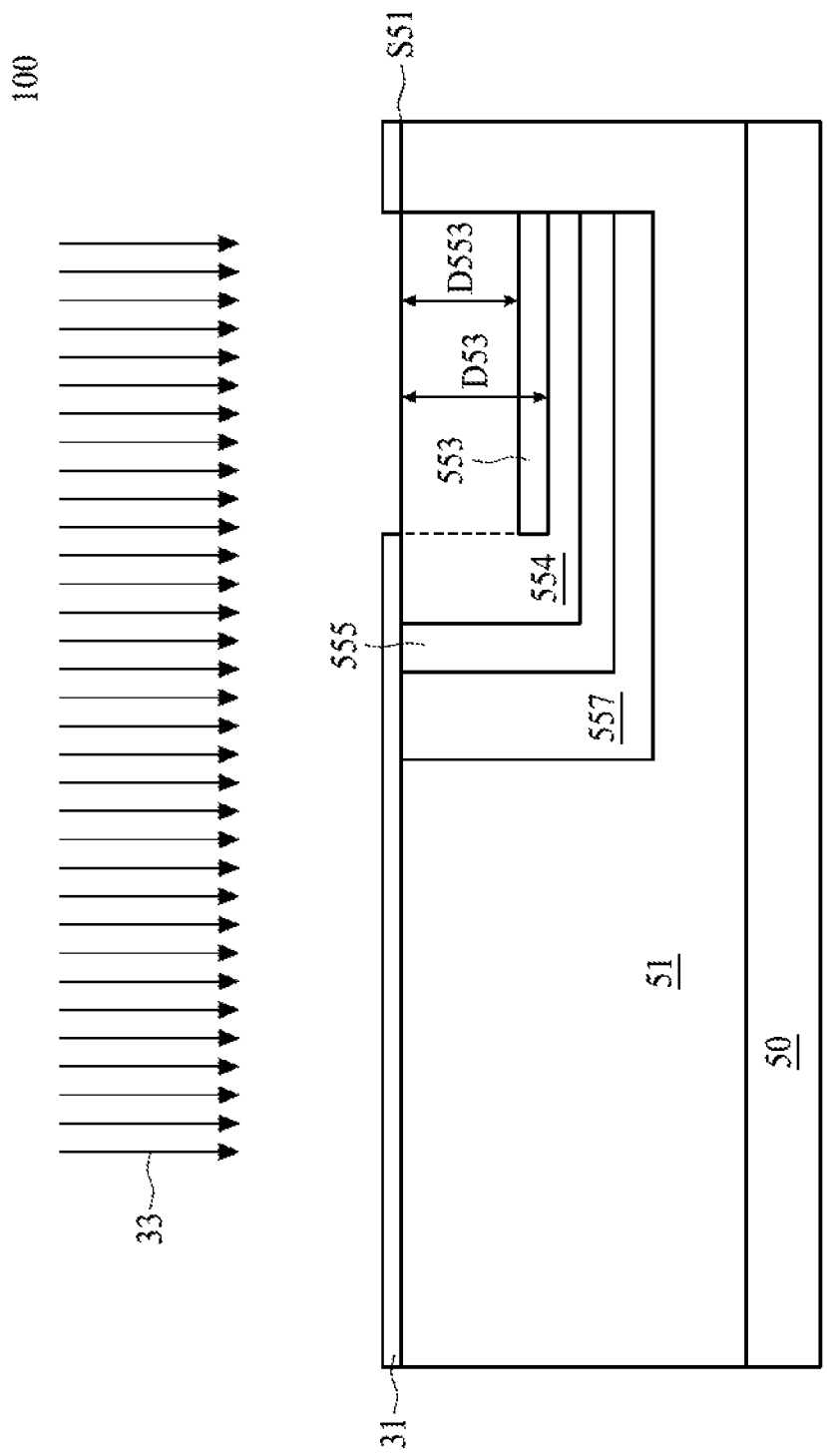

In FIG. 24, ion implantation 33, including a forth predetermined energy, implants dopants into region 554 so as to form a horizontal portion of region 553 above the horizontal portion of region 555. The horizontal portion of region 553 is under the surface S51 by a depth D553. The dopants are implanted from a depth D53 up to the depth D533. In some embodiments, the dopants are of a same type as the region 555, such as a positive-type. The resist 31 is stripped after the horizontal portion of region 553 is formed. Region 554 above region 555 includes the dopants of an opposite conductive type to region 553, such as negative dopants.

Figure 25:
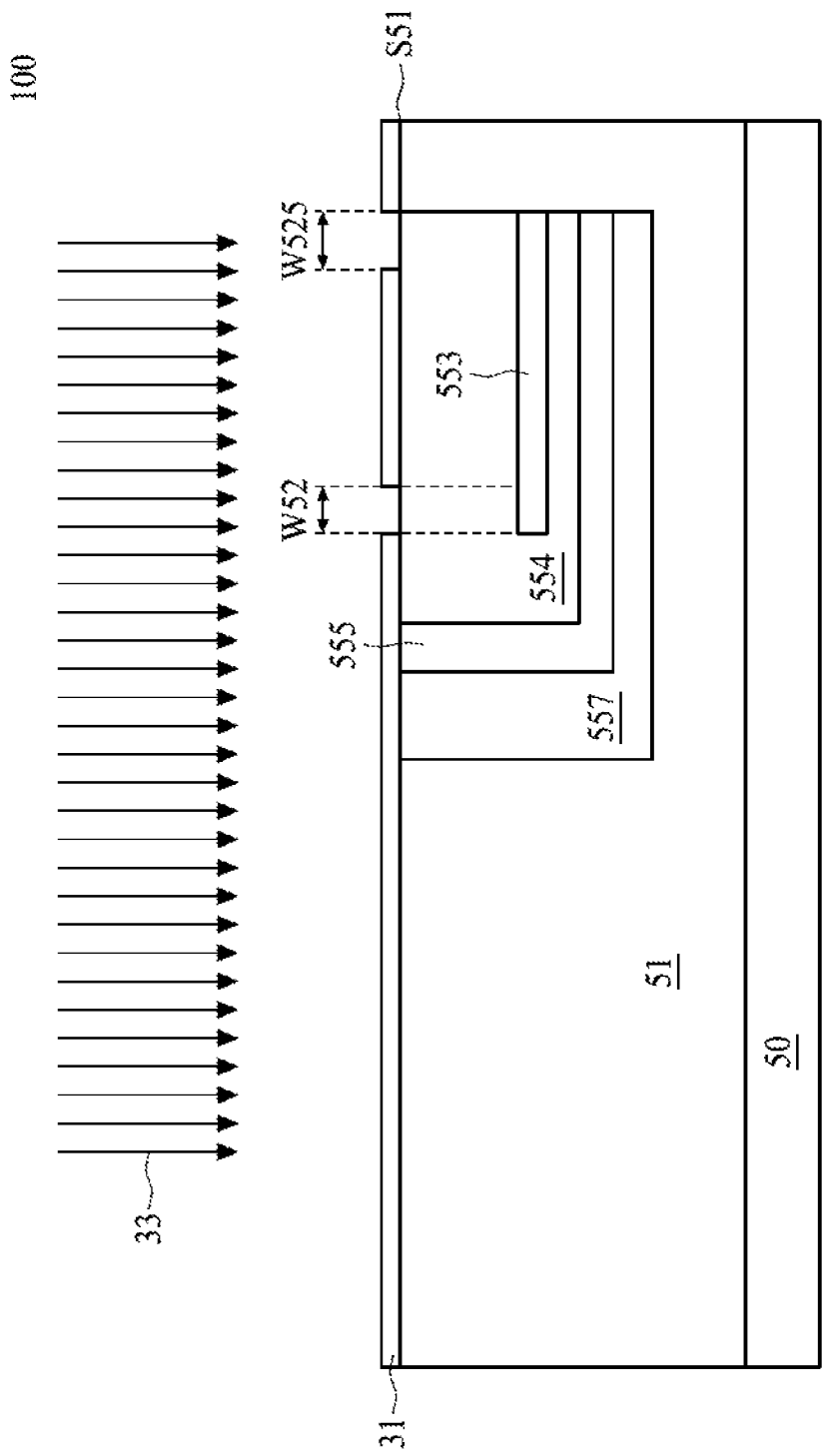

In FIG. 25, another resist 31 with a width W525 of a first opening well and a width W52 of a second opening well is partially covering region 554 over the horizontal portion of region 553. The first and the second opening wells expose underlying region 554 to another ion implantation 33. The first opening well is aligned to an end of region 553. The second opening well is aligned to another end between region 553 and the epitaxy region 51.

Figure 26:
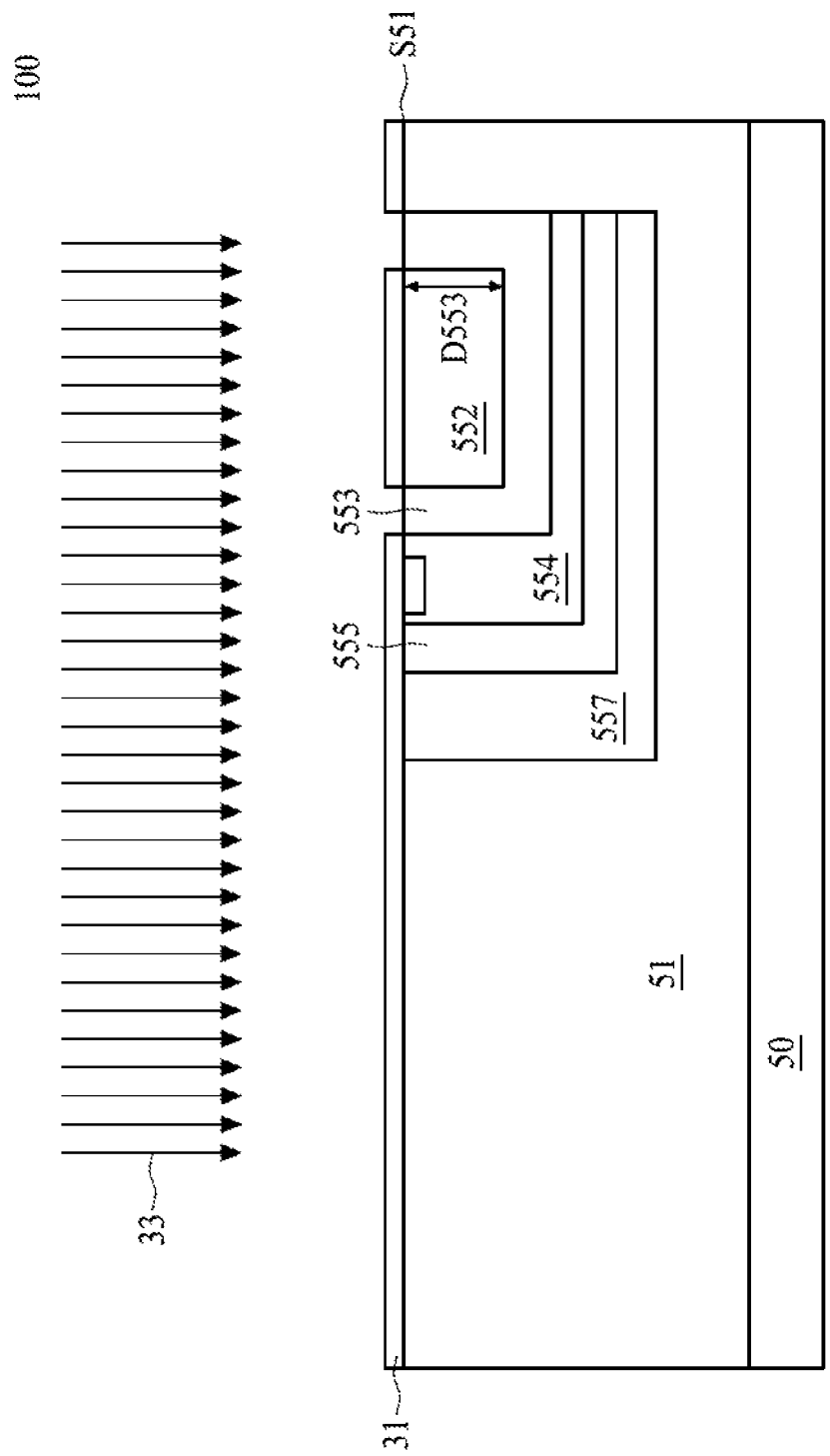

In FIG. 26, ion implantation 33, including a fifth predetermined energy, implants dopants into region 554 so as to form a lateral portion of region 553 above the horizontal portion of region 553. The lateral portion of region 553 includes a depth D553. The dopants are implanted from the depth D553 up to the surface S51. In some embodiments, ion implantation 33 in FIG. 26 includes multiple operations of implantation with a variety of ion energies. In some embodiments, the dopants are of a same type as the region 555, such as a positive-type. The resist 31 is stripped after the lateral portion of region 555 is formed. Region 552 partially surrounded by region 553 includes the dopants of an opposite conductive type to region 553, such as negative dopants.

Figure 27:
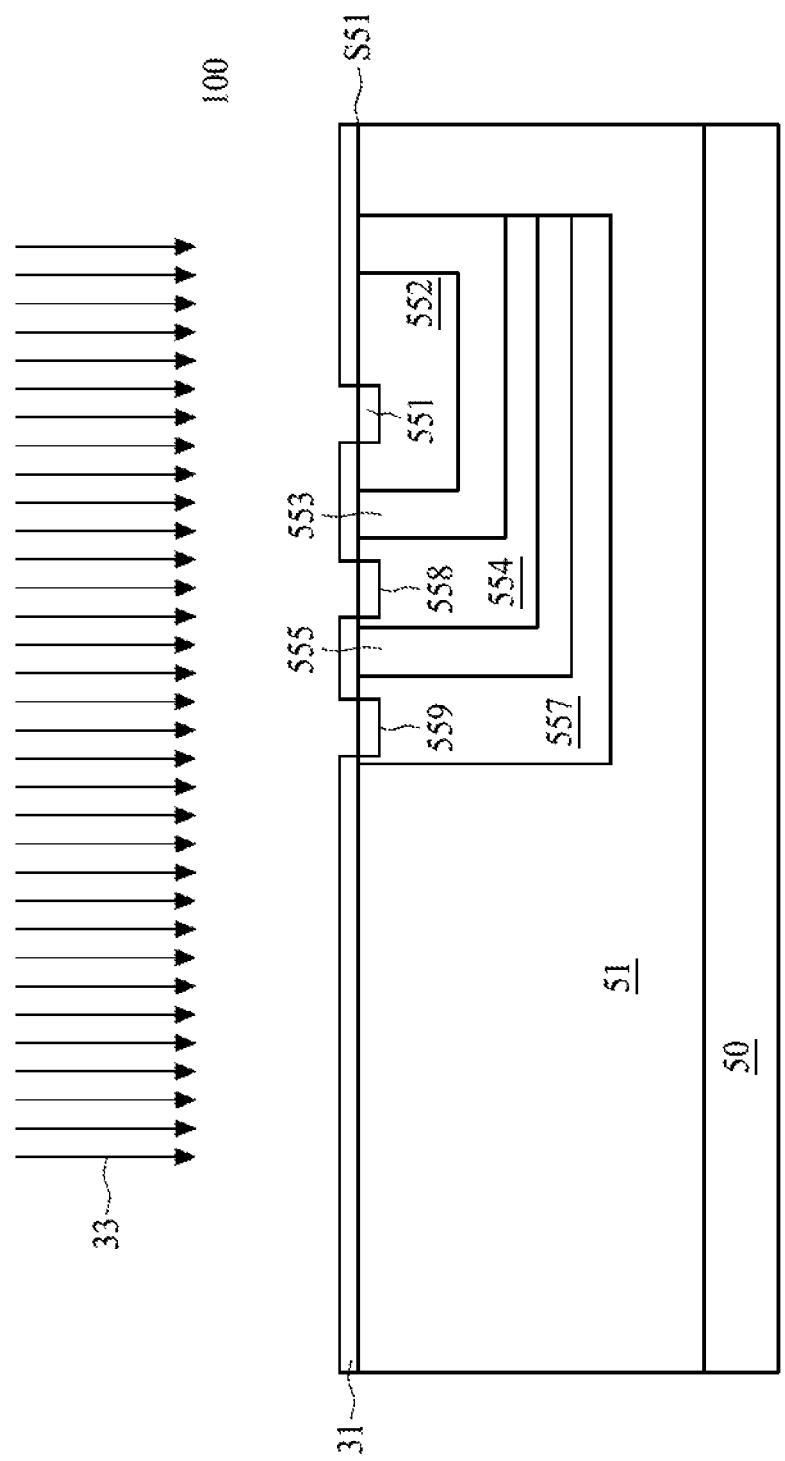

In FIG. 27, heavily doped regions 551, 558, and 559 are formed. In FIG. 27, another resist 31 with three opening wells is partially covering regions 552, 554, and 557. The three opening wells expose underlying regions 552, 554, and 557 to another ion implantation 33.

Ion implantation 33 implants dopants into regions 552, 554, and 557 to form heavily doped regions 551, 558, and 559. In some embodiments, the dopants are of a same type as the region 557, 555, or 552, such as a negative-type. The dopant concentration is substantially greater than that in regions 552, 554, and 557. The resist 31 is stripped after the heavily doped regions 551, 558, and 559 are formed.

Figure 28:
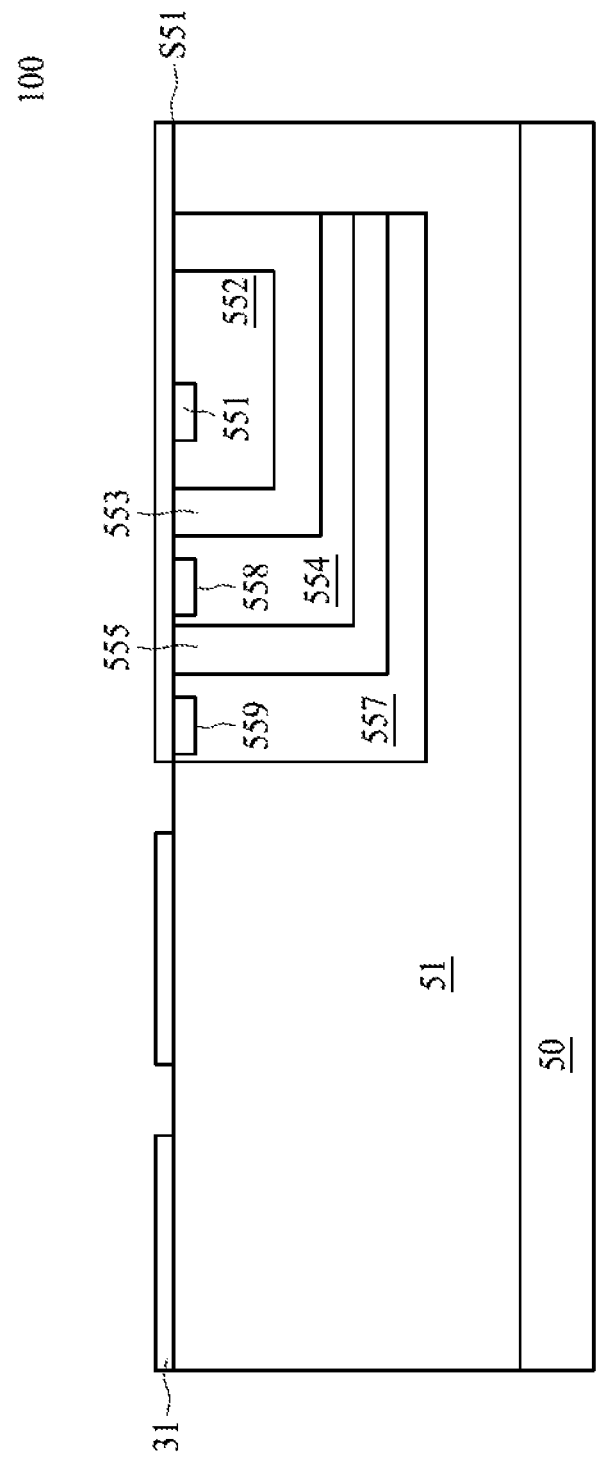

In FIG. 28, a resist 31, including a pattern for forming isolations, is covered over the surface S51.

Figure 29:
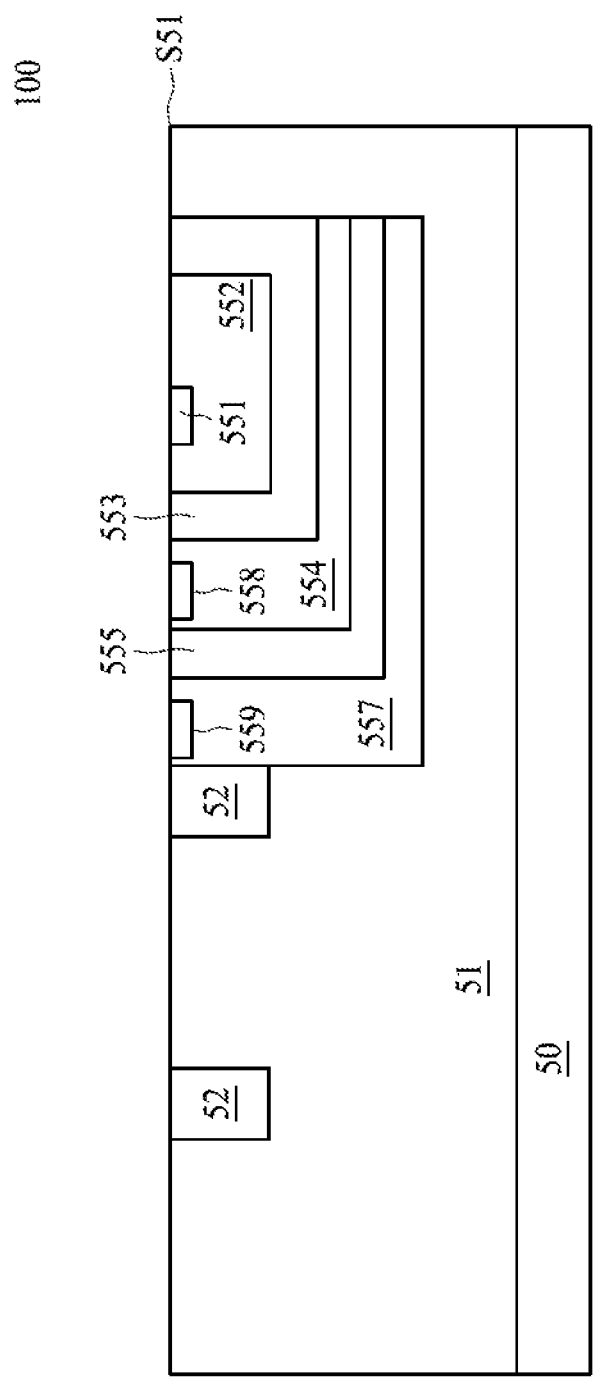

In FIG. 29, the epitaxy region 51 includes the isolation region 52 formed by etching a trench in the epitaxy region 51 on the surface S51 and filling the trench with insulator materials, such as silicon oxide, silicon nitride, or silicon oxynitride.

Figure 30:
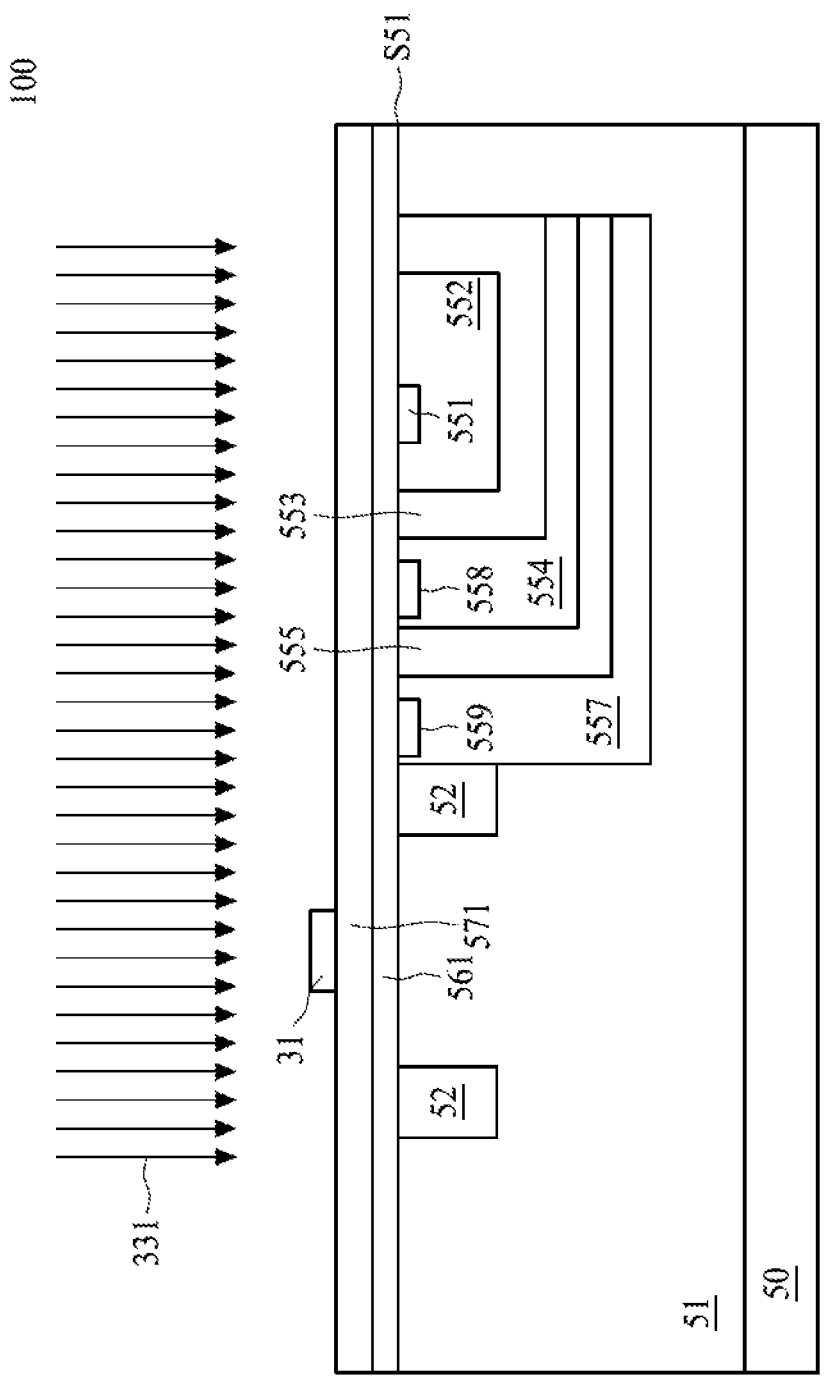

In FIG. 30, a gate dielectric, layer 561 is covering over the surface S51. In an embodiment, the gate dielectric layer 561 is a thin film formed by a suitable deposition process. A gate electrode layer 571 is covering on top of the gate dielectric layer 561. In an embodiment, the gate dielectric layer 561 and the gate electrode layer 571 are sequentially deposited over the surface S51 by some deposition processes. In some embodiments, the gate dielectric layer 561 and the gate electrode layer 571 are only deposited over a predefined region for forming transistor structures. The gate electrode layer 571 is made of any suitable material, such as polysilicon.

The gate dielectric layer 561 and the gate electrode layer 571 are patterned by a lithographic process. In some embodiments, the gate dielectric layer 561 is patterned after the gate electrode layer 571 is patterned. In some embodiments, the lithographic process is a photolithographic process.

Figure 31:
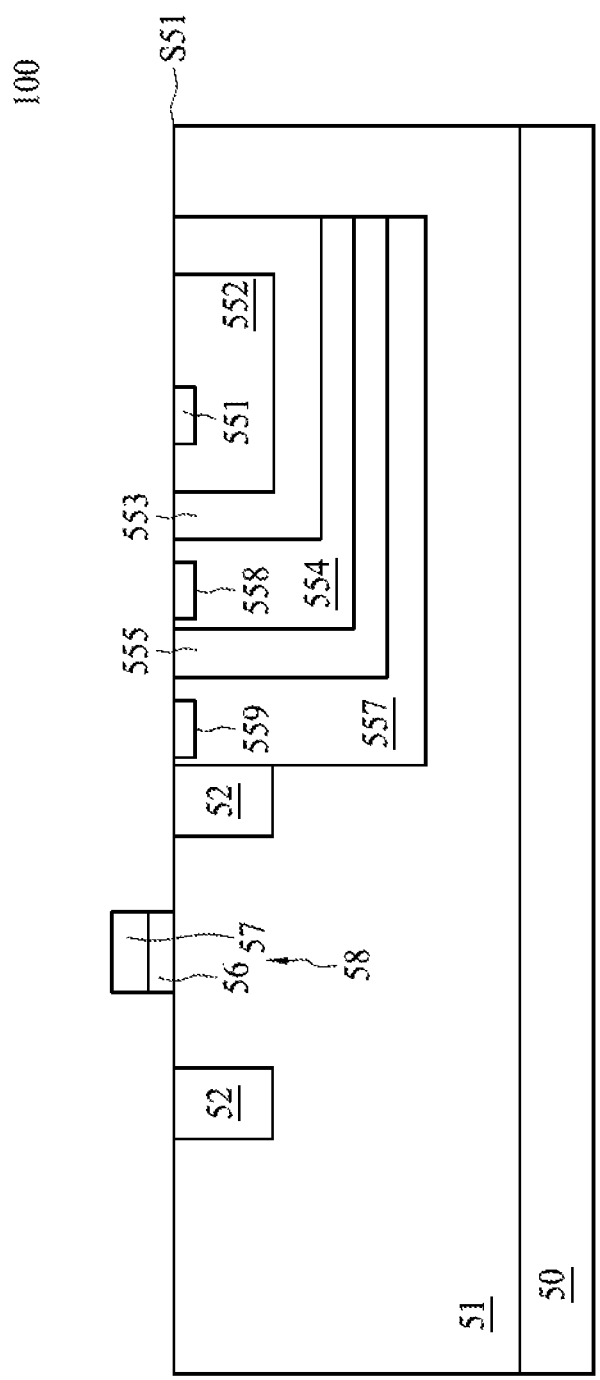

In FIG. 31, the resist feature is transferred to form a gate structure 58 on the surface S51 and in between isolation regions 52. The gate structure 58 includes a gate electrode 57 and a gate dielectric 56.

Figure 32:
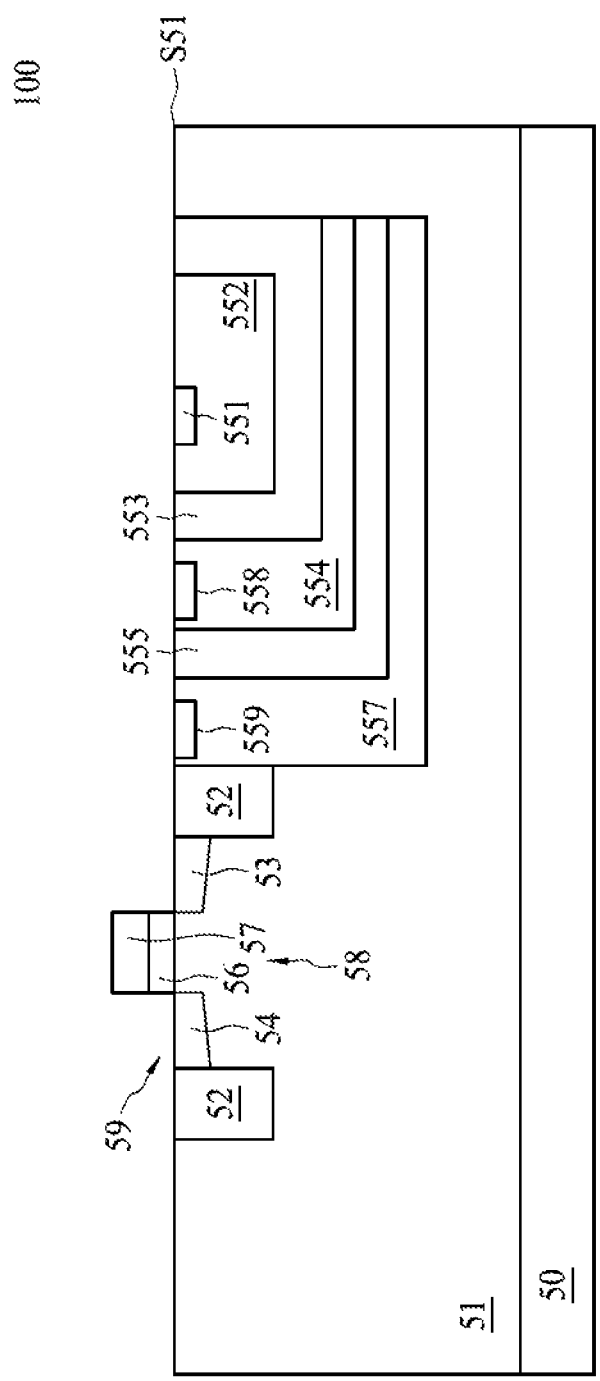

In FIG. 32, in some embodiments, a source region 53 or a drain region 54 is formed by ion implantation or epitaxially growth. Ion implantation or epitaxial growth introduces dopants in the source region 53 or the drain region 54. In various embodiments, the source region 53 or the drain region 54 has different doping profiles formed by a multi-process implantation.

Figure 33:
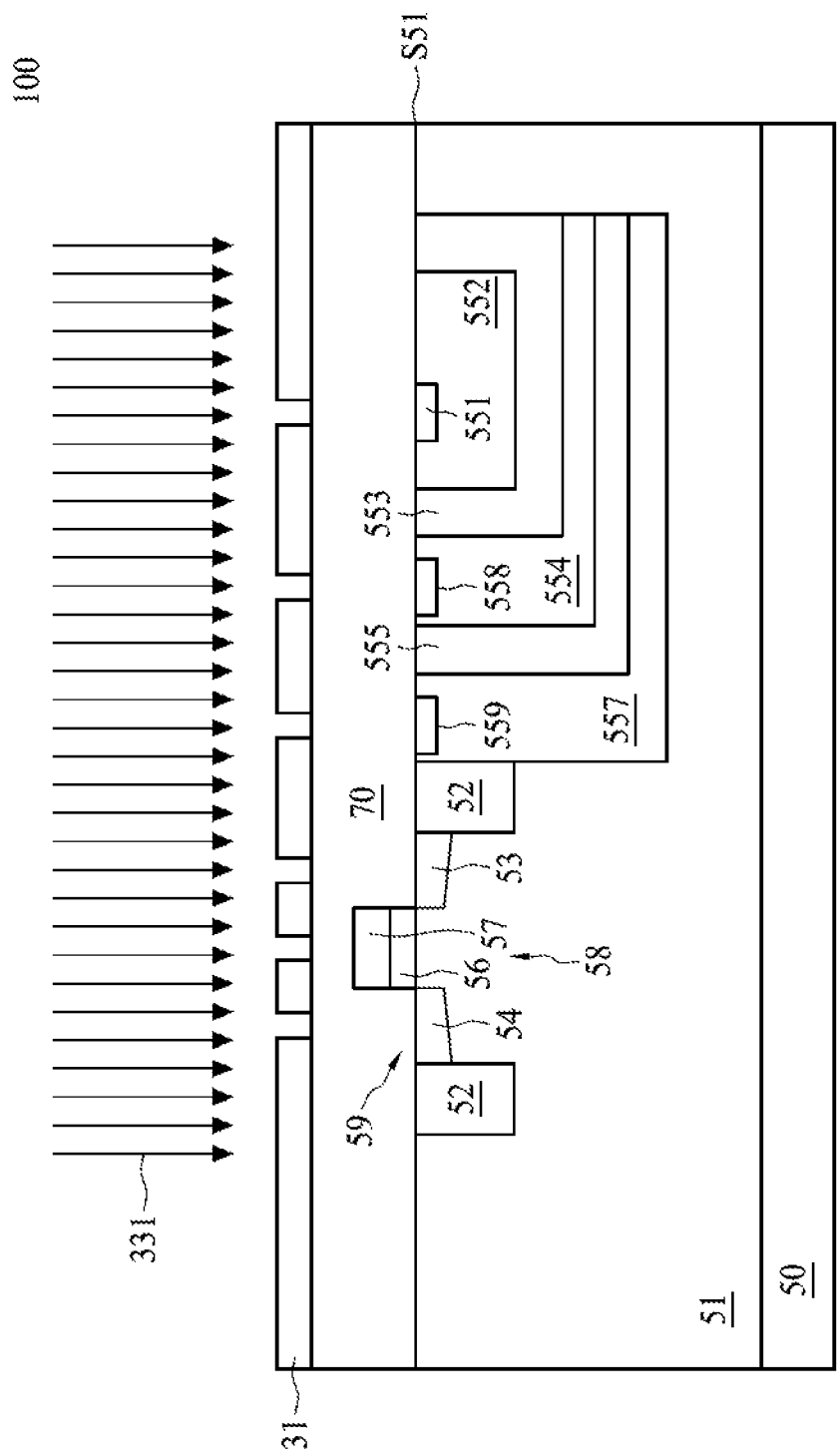

In FIG. 33, the dielectric layer 70 is covering over the surface S51 by any suitable process, such as a deposition process. The dielectric layer 70 is in contact with the gate structure 58. A resist 31 is formed on top of the dielectric layer 70. An etching operation 331 is performed to transfer a patterned resist feature to the dielectric layer 70.

Figure 34:
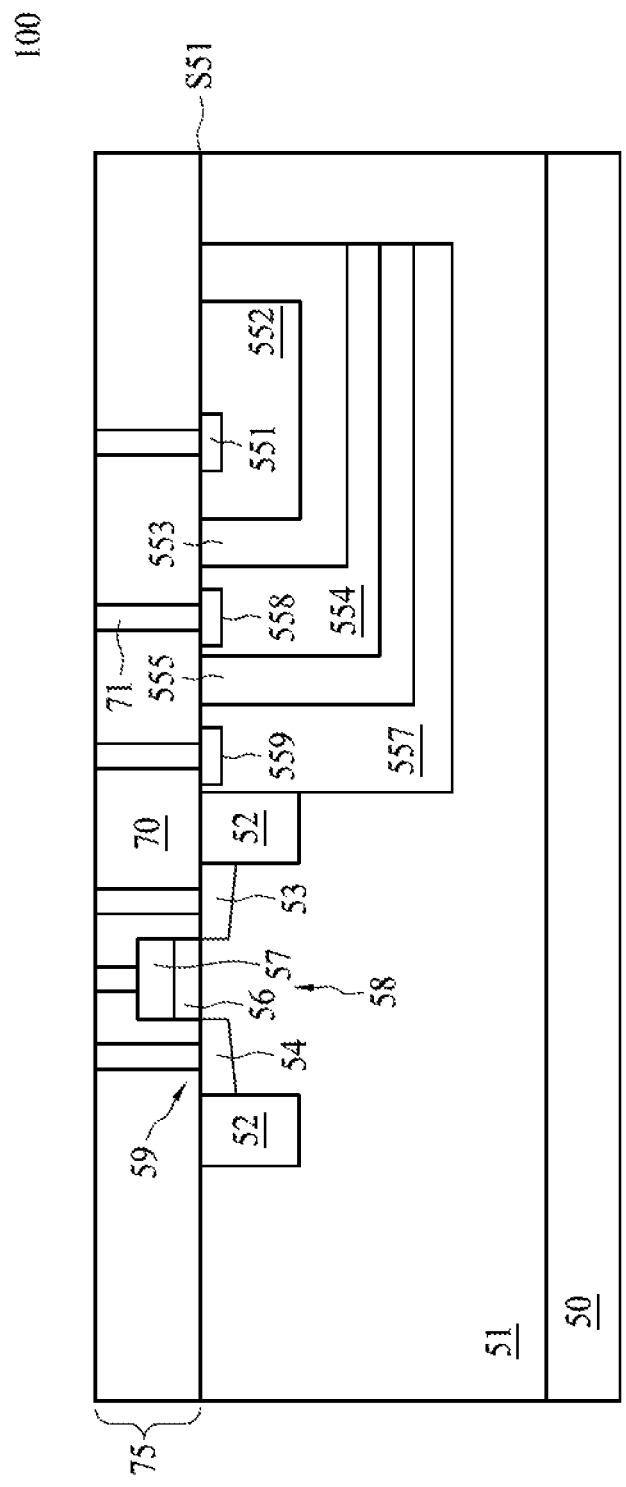

In FIG. 34, the patterned resist feature is transferred to the dielectric layer 70 in order to form trenches. In some embodiments, the trenches are formed by any suitable etching process, such as selective etching, dry etching, and/or a combination thereof. The trenches are filled by conductive materials to form contacts 71. The contacts 71 are formed by filling the trenches by suitable processes, such as a deposition process. The contacts 71 are electrically connect with the gate structure 58, the source region 53, the drain region 54, and the heavily doped regions 559, 558, and 551. A depth of the contacts 71 is controlled by adjusting process parameters in a CVD process. The process parameters include a total pressure, reactant concentrations, deposition temperature, or a deposition rate.

Figure 35:
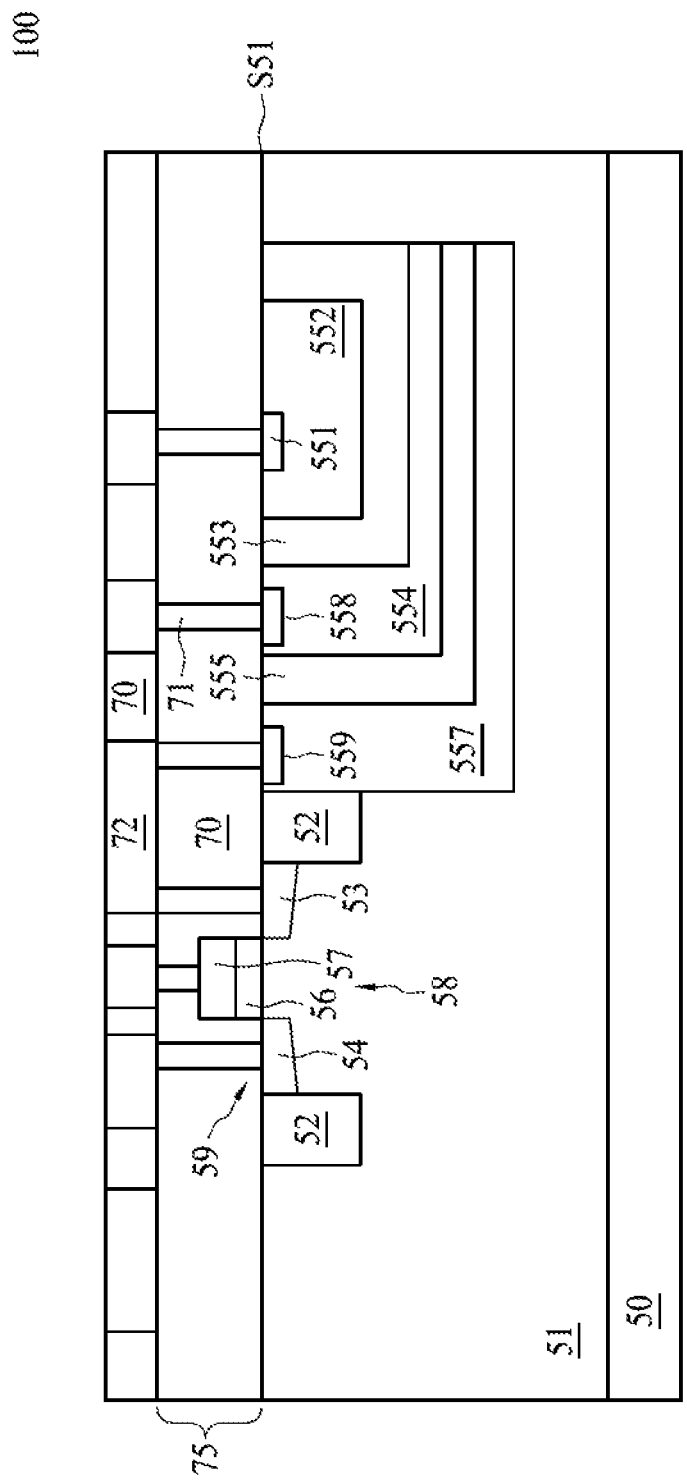

In FIG. 35, a conductive layer is deposited and patterned by transferring a resist feature to the conductive layer. The resist feature is transferred to the conductive layer to form recesses and the metal line 72. The recesses are filled by dielectric materials to form another dielectric layer 70 over the ILD layer 75. The metal lines 72 are between the dielectric layer 70.

Figure 36:
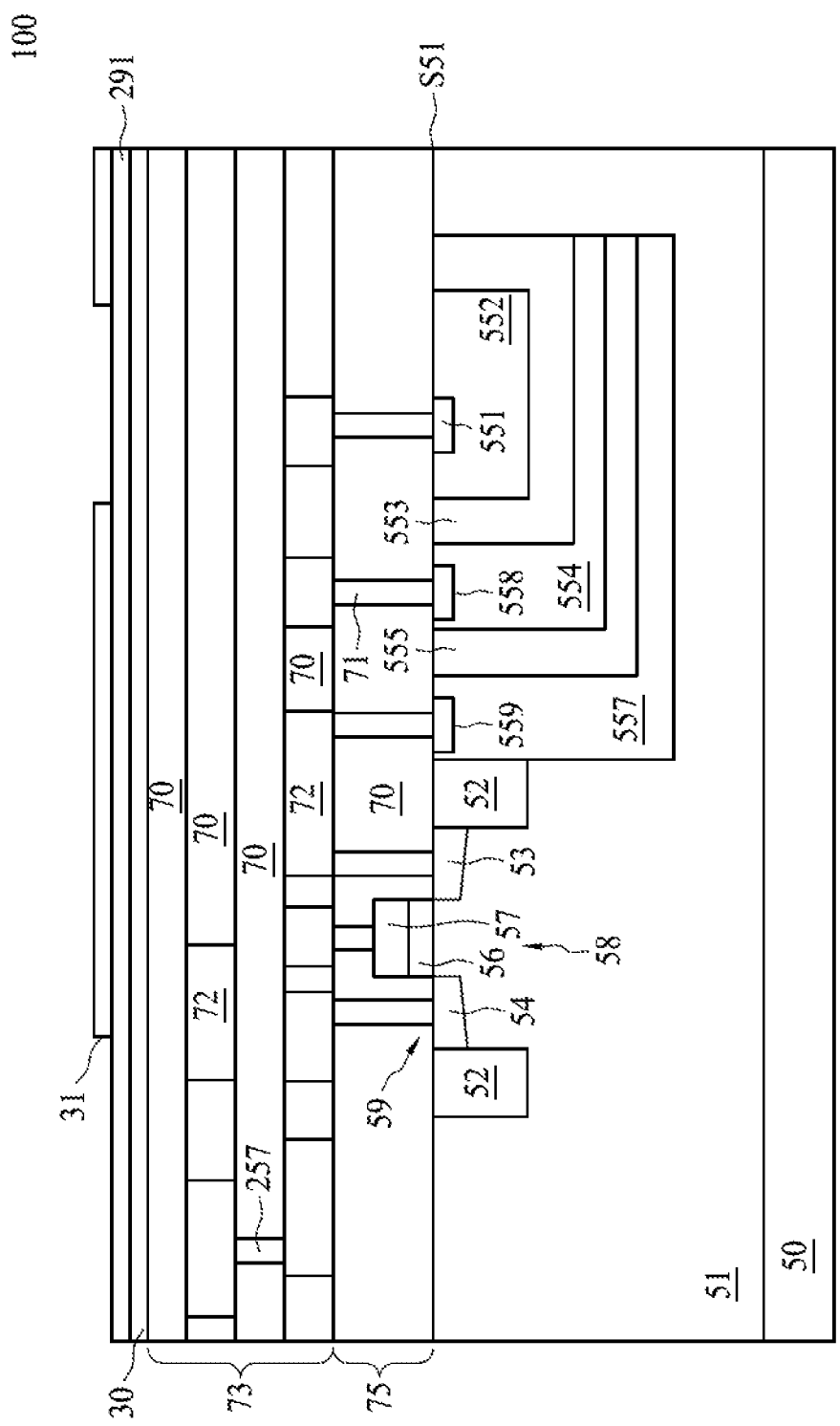

In FIG. 36, multiple layers of metal lines 72 and dielectric layers 70 are deposited and etched to form the interconnect region 73. In some embodiments, a via structure 257 in the interconnect region 73 are formed to connect metal lines in different layers.

The filter layer 30 is blanket formed over the interconnect region 73 by any suitable process, such as deposition. The conductive layer 291 is blanket formed over the filter layer 30 by any suitable process, such as deposition. The resist 31 is covering the conductive layer 291 to transfer a resist pattern to the conductive layer 291 by any suitable lithographic process.

Figure 37:
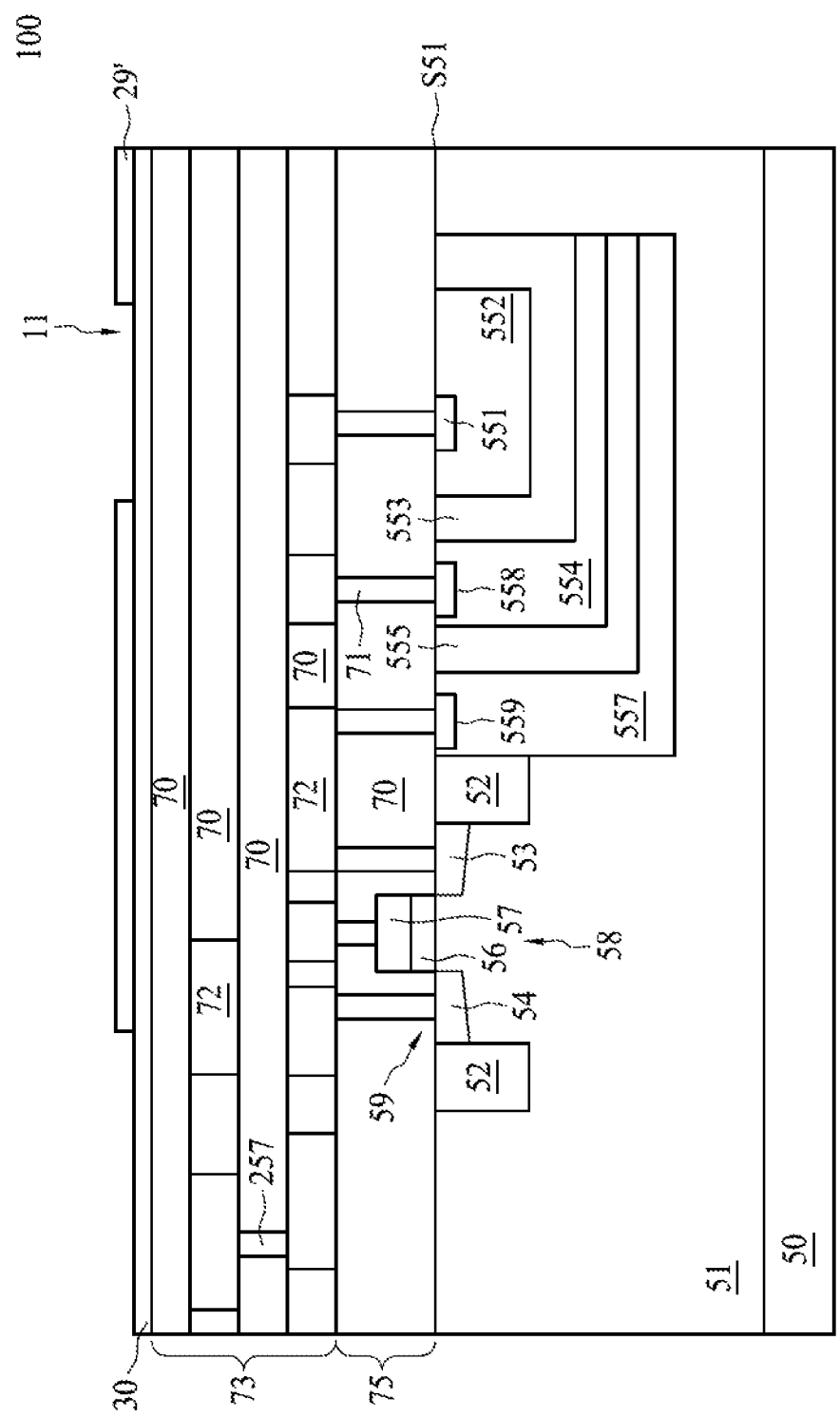
Figure 38:
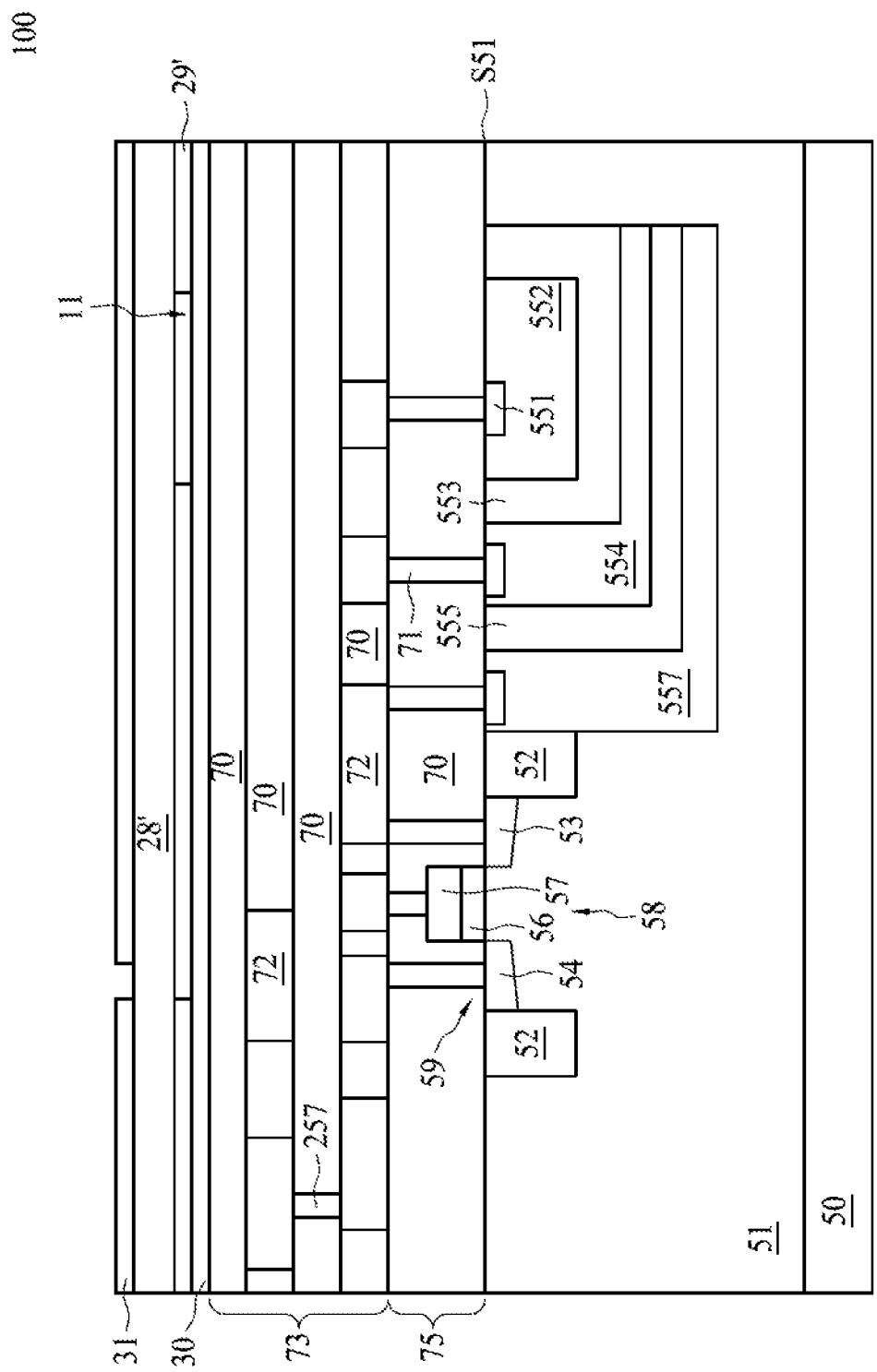

In FIG. 37, the conductive layer 29' is formed with the aperture 11. In FIG. 38, the dielectric layer 28' is blanket formed on top of the conductive layer 29' such that the aperture 11 is filled. The resist 31 is covering the dielectric layer 28' so as to transfer a resist pattern to the dielectric layer 28' by any suitable lithographic process.

Figure 39:
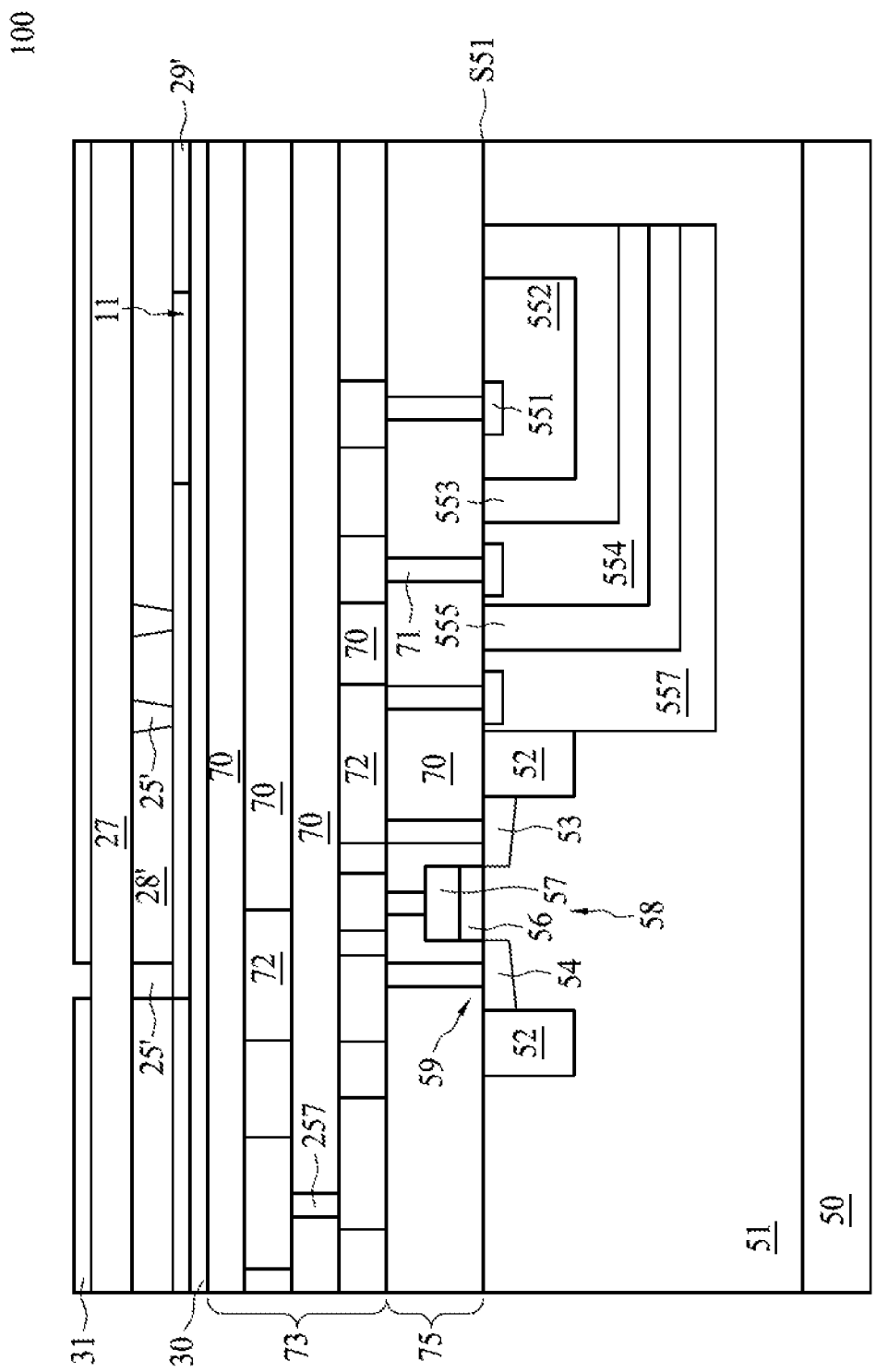

In FIG. 39, the dielectric layer 28' is formed with recesses by the suitable lithographic process. The recess is filled by any suitable material, such as conductive material, to form the via structure 25' within the dielectric layer 28'. The dielectric layer 27 is blanket formed over the dielectric layer 28' and the via structure 25' such that a top of the via structure 25' is covered by the dielectric layer 27. The dielectric layer 27 is composed of material with the first refractive index higher than the second refractive index of the dielectric, layer 28'. The resist 31 is covering the dielectric layer 27 so as to transfer a resist pattern to the dielectric layer 27 by any suitable lithographic process.

Figure 40:
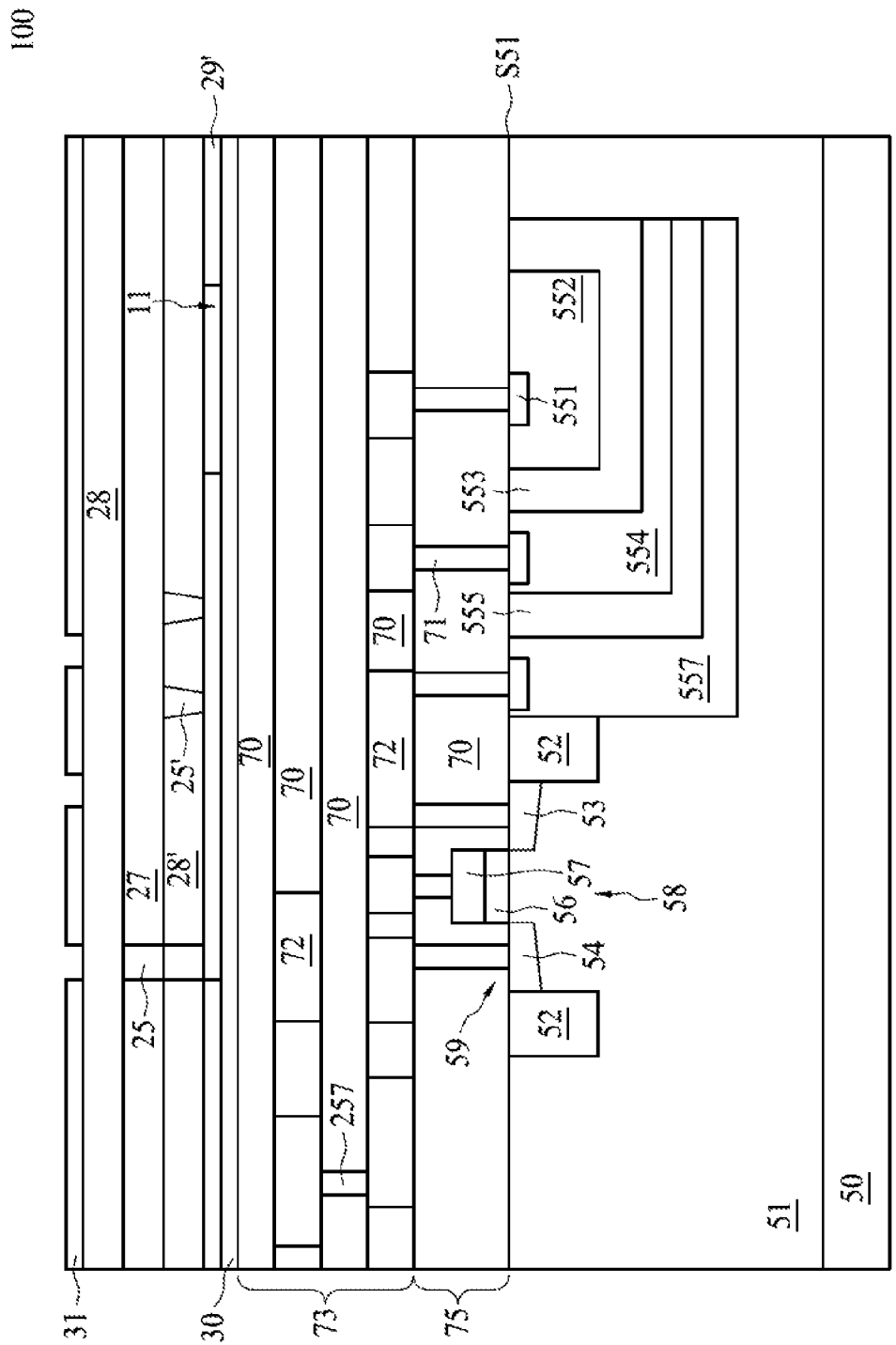

In FIG. 40, the dielectric layer 27 is formed with recesses by the suitable lithographic process. The recess is filled by any suitable material, such as conductive material, to form the via structure 25 within the dielectric layer 27. A second dielectric layer 28 is blanket formed over the dielectric layer 27. The resist 31 is covering the second the dielectric layer 28 so as to transfer a resist pattern to the second dielectric layer 28 by any suitable lithographic process.

Figure 41:
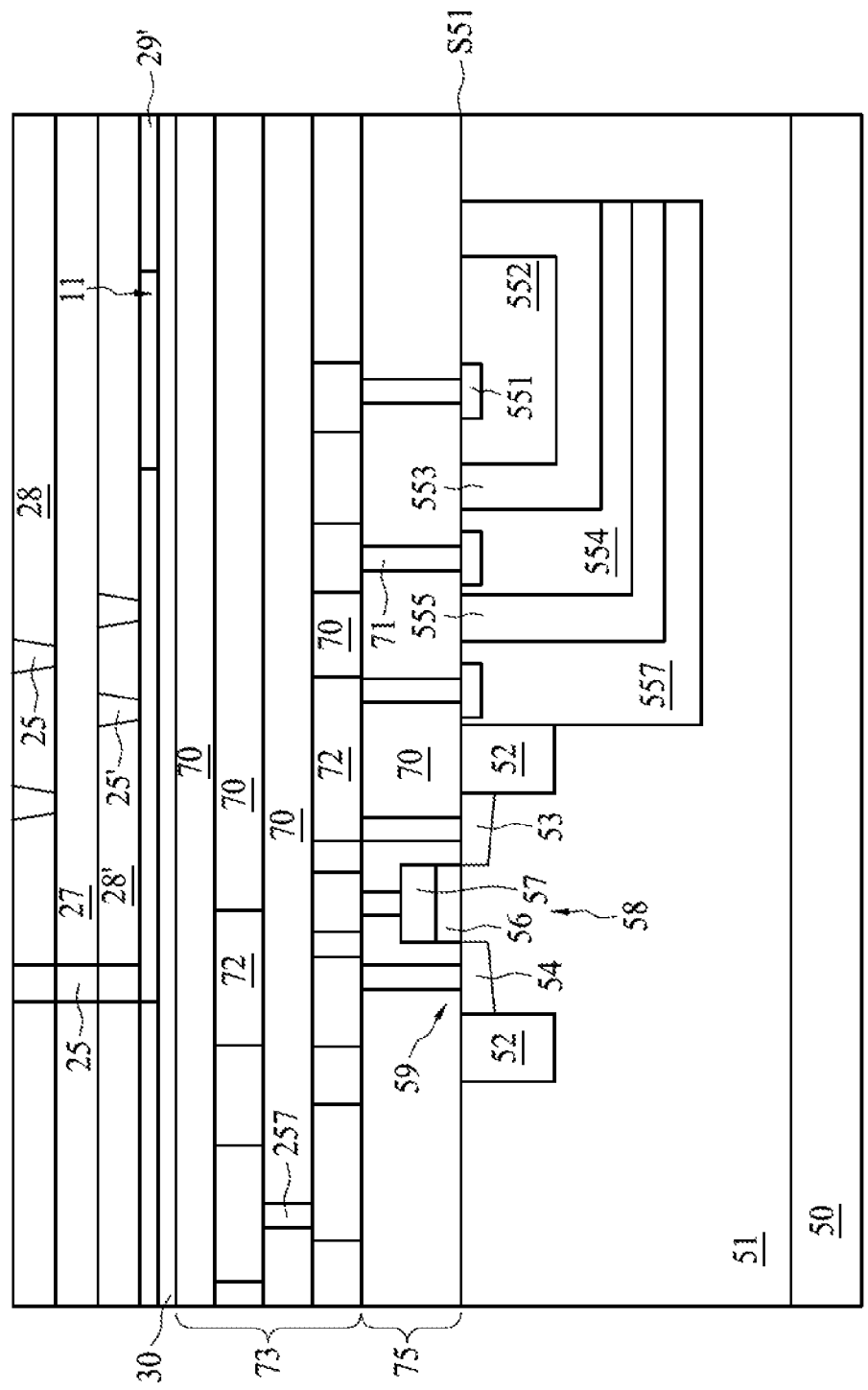
Figure 42:
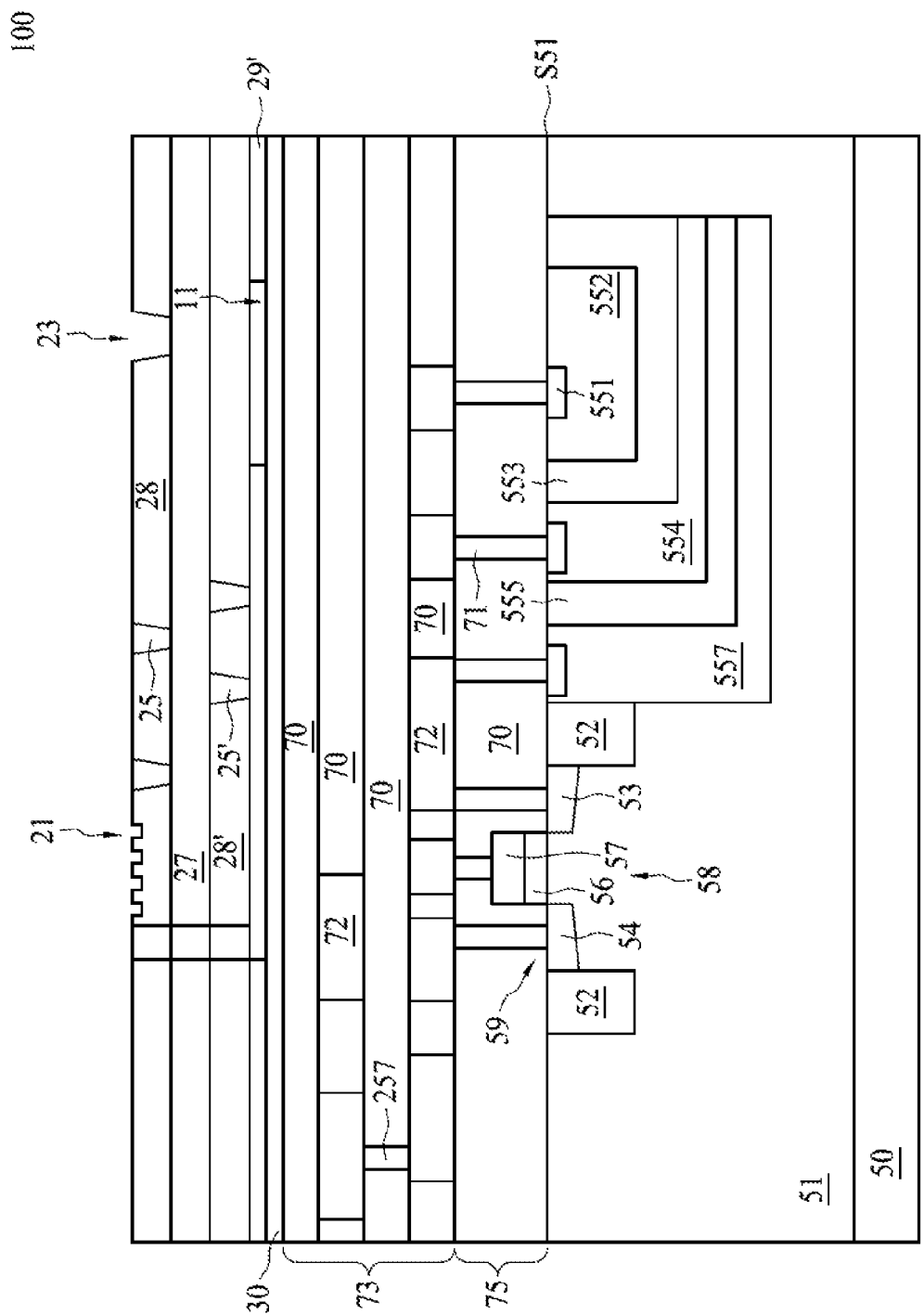

In FIG. 41, the second dielectric layer 28 is patterned and filled with the via structure 25. In FIG. 42, a second dielectric, layer 28 is patterned to form the grating of the grating structure 21 by any suitable process, such as photolithography. The grating is an optical grating in the second dielectric layer 28. In some embodiments, the dielectric layer 27 is patterned to form the optical grating, and the second dielectric layer 28 is etched to expose the optical grating underneath the second dielectric layer 28. The second dielectric layer 28 is patterned to form the recess of the sample holding portion 23.

Figure 43:
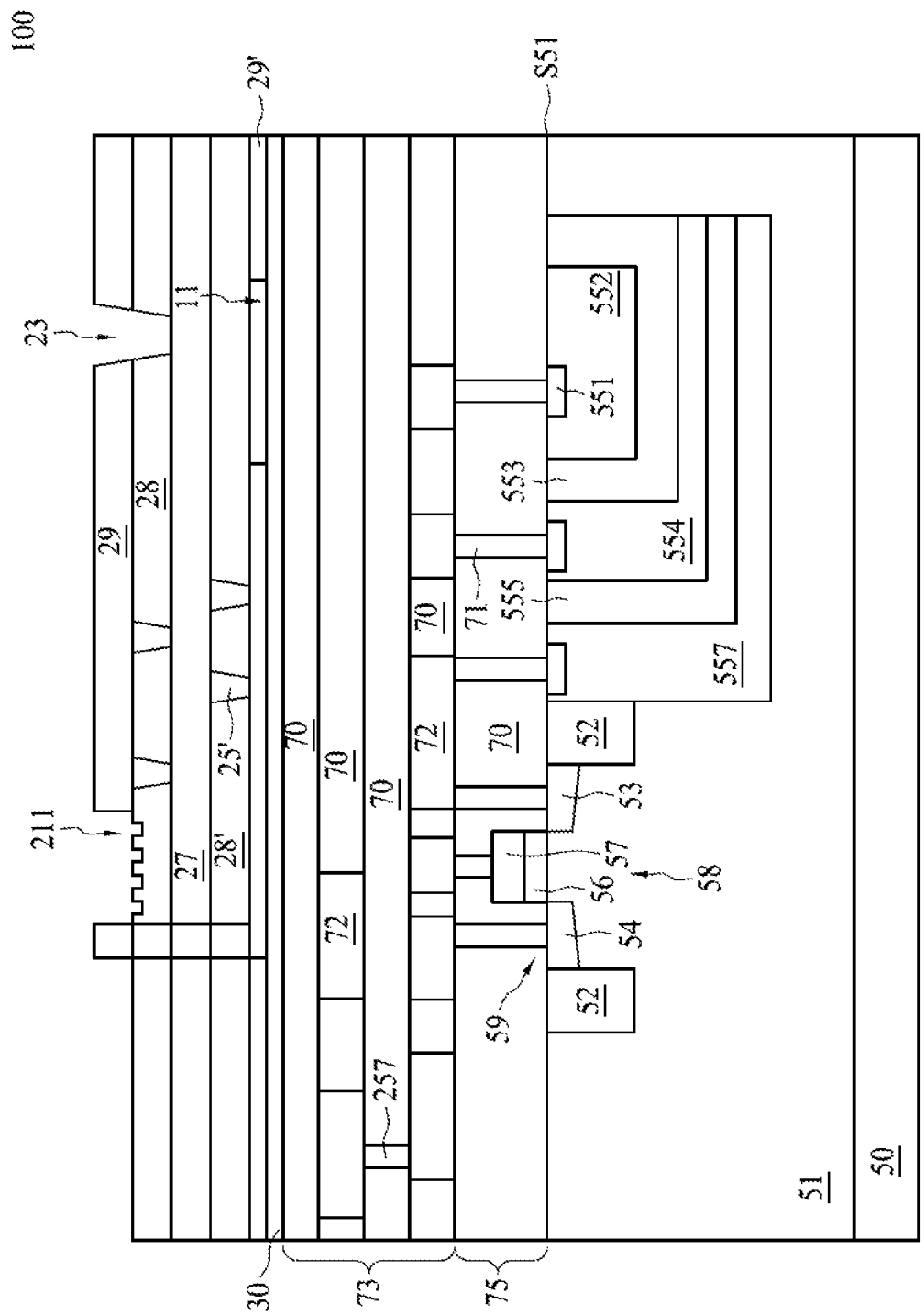

In FIG. 43, a second conductive layer 29 is blanket formed over the second dielectric layer 28. The second conductive layer 29 is patterned to include the opening well 211 so as to expose the grating of the grating structure 21. The second conductive layer 29 is etched to form the recess of the sample holding portion 23 such that the recess of the sample holding portion 23 passes through the second conductive layer 29 and the second dielectric layer 28. The opening well of the recess is over the dielectric layer 27. In some embodiments, the second conductive layer 29 and an underlying second dielectric layer 28 are etched by suitable processes, such as a selective etching, a dry etching, and/or combination thereof.

Figure 44:
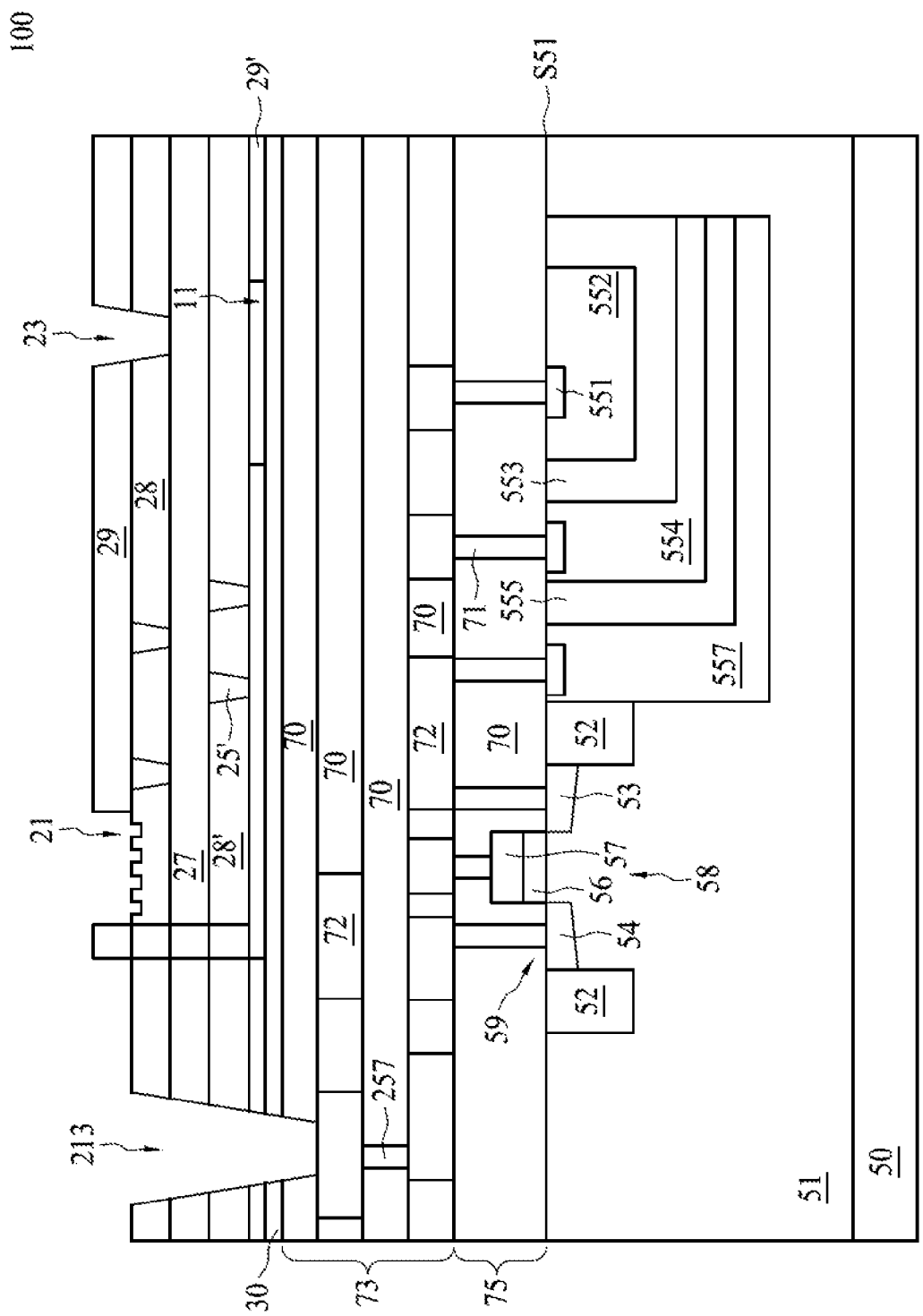

In FIG. 44, a recess 213 is formed by any suitable etching process to etch the second dielectric layer 28, the dielectric layer 27, the dielectric layer 28, the conductive layer 29, the filter layer 30, and the dielectric layer 70 such that the pad 22 is exposed. In some embodiments, the pad 22 is to be connected to other external circuitry.

Some embodiments of the present disclosure provide an optical sensor. The optical sensor includes a semiconductive substrate. A light sensing region is on the semiconductive substrate. A waveguide region is configured to guide light from a wave insert portion through a waveguide portion and to a sample holding portion. The waveguide portion includes a first dielectric layer including a first refractive index. A second dielectric layer includes a second refractive index. The second refractive index is smaller than the first refractive index. A first interconnect portion is positioned in the waveguide portion, configured to transmit electrical signal from the light sensing region to an external circuit. The sample holding portion is over the light sensing region.

Some embodiments of the present disclosure provide an optical sensor. The optical sensor includes a semiconductive substrate. A dielectric layer is over the semiconductive substrate. A reflective structure is in the dielectric layer. A waveguide region is configured to guide light from a wave insert portion through a waveguide portion and to a sample holding portion. The waveguide portion includes the dielectric layer and the reflective structure. A light sensing region is over the semiconductive substrate.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A semiconductor device, comprising:
a semiconductive substrate;
a dielectric layer over the semiconductive substrate;
a reflective structure in the dielectric layer;
a waveguide region configured to guide light from a wave insert portion through a waveguide portion and to a sample holding portion, and the waveguide portion comprising the dielectric layer and the reflective structure;
an interconnect region below the waveguide region, and the interconnect region being disposed above the light sensing region; and
a light sensing region over the semiconductive substrate, and the waveguide region disposed above the light sensing region,
wherein the reflective structure in the dielectric layer is not electrically connected to the light sensing region.

2. The semiconductor device of claim 1, wherein the light sensing region comprises a multi-junction photodiode.

3. The semiconductor device of claim 1, further comprising a filter layer between the interconnect region and the waveguide region.

4. The semiconductor device of claim 1, wherein the wave insert portion comprises a grating.

5. The semiconductor device of claim 1, wherein the dielectric layer comprises a core layer and a cladding layer.

6. The semiconductor device of claim 5, wherein a ratio between a total area of the core layer and a total area of the reflective structure in the cladding layer at an interface between the core layer and the cladding layer is greater than about 10.

7. The semiconductor device of claim 1, wherein the dielectric layer comprises a plurality of layers having at least two different refractive indices.

8. The semiconductor device of claim 1, wherein the sample holding portion is surrounded by a portion of the dielectric layer.

* * * * *